(12) United States Patent
Ijiro et al.

(10) Patent No.: US 9,447,316 B2
(45) Date of Patent: Sep. 20, 2016

(54) PARTICLE AGGREGATE, MANUFACTURING METHOD FOR PARTICLE AGGREGATE, FLUORESCENCE ENHANCING ELEMENT, AND DEVICE USING PHOTOCHEMICAL REACTIONS

(75) Inventors: Kuniharu Ijiro, Sapporo (JP); Kenichi Niikura, Sapporo (JP); Naoki Iyo, Sapporo (JP); Takashi Nishio, Sapporo (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 283 days.

(21) Appl. No.: 14/000,749

(22) PCT Filed: Feb. 22, 2012

(86) PCT No.: PCT/JP2012/054279
§ 371 (c)(1),
(2), (4) Date: Dec. 3, 2013

(87) PCT Pub. No.: WO2012/115151
PCT Pub. Date: Aug. 30, 2012

(65) Prior Publication Data
US 2014/0077132 A1 Mar. 20, 2014

(30) Foreign Application Priority Data
Feb. 22, 2011 (JP) .................. 2011-036468

(51) Int. Cl.
*C09K 11/02* (2006.01)
*B22F 1/00* (2006.01)
(Continued)

(52) U.S. Cl.
CPC .......... *C09K 11/025* (2013.01); *B22F 1/0051* (2013.01); *B22F 1/02* (2013.01); *B82Y 30/00* (2013.01); *C07C 323/12* (2013.01); *C07F 1/12* (2013.01)

(58) Field of Classification Search
None
See application file for complete search history.

(56) References Cited

U.S. PATENT DOCUMENTS 5,888,290 A * 3/1999 Engle .................. B82Y 30/00
106/287.12

FOREIGN PATENT DOCUMENTS

JP 09-000913 1/1997
JP 2008-285753 11/2008
(Continued)

OTHER PUBLICATIONS

Kim et al. "Fabrication of Hollow Palladium Spheres and Their Successful Application to the Recyclable Heterogenous Catalyst for Suzuki Coupling Reactions." J. Am. Chem. Soc. 2002, 124, 7642-7643.
(Continued)

*Primary Examiner* — Alexandre Ferre
(74) *Attorney, Agent, or Firm* — K&L Gates LLP; Louis C. Cullman; Michelle Glasky Bergman

(57) ABSTRACT

Provided is a hollow particle aggregate formed by aggregating a plurality of self-organizable particles, wherein a metal core is modified by a surface modifier for a metal core comprising a first segment comprising an optionally branched fluorinated alkylene glycol group, an optionally branched fluorinated alkylene group, or an optionally branched fluorinated azaalkylene group; a second segment comprising at least one hydrophilic group and bonding to one of the ends of a main chain of the first segment; and a functional group that bonds directly or indirectly to the another end of the main chain of the first segment and is able to bond to the metal core.

11 Claims, 12 Drawing Sheets

(51) Int. Cl.
  *B22F 1/02*     (2006.01)
  *C07C 323/12*   (2006.01)
  *B82Y 30/00*    (2011.01)
  *C07F 1/12*     (2006.01)

(56)            References Cited

FOREIGN PATENT DOCUMENTS

JP    2009-020437    1/2009
  WO    2010/068531    6/2010

OTHER PUBLICATIONS

Patra et al. "Colloidal Microcapsules: Self-Assembly of Nanoparticles at the Liquid-Liquid Interface." Chem. Asian J. 2010, 5, 2442-2453.

Shibu et al. "Gold Nanoparticle Superlattices: Novel Surface Enhanced Raman Scattering Active Substrates." Chem. Mater. 2009, 21, 3773-3781.

Sun et al. "Polymer Mediated Self-Assembly of Magnetic Nanoparticles." J. Am. Chem. Soc. 2002, vol. 124, No. 12.

Zhang et al. "Polydisperse Aggregates of ZnO Nanocrystallites: A Method for Energy-Conversion-Efficiency Enhancement in Dye Sensitized Solar Cells." Adv. Funct. Mater. 2008, 18, 1654-1660.

Nishio, et al. "Self-lubricating nanoparticles: self-organization into 3D-superlattices during a fast drying process" Chemical Communications, 46, 8977, epub Oct. 22, 2010.

Gentilini, et al. "Water-Soluble Gold Nanoparticles Protected by Fluorinated Amphiphilic Thiolates" Journal of the American Chemical Society (JACS) Articles, Nov. 19, 2008, 15678-15682.

Snow, et al. "Fluorine-labeling as a diagnostic for thiol-ligand and gold nanocluster self-assembly" Analyst, 1790, Fifrst Published Jul. 10, 2009.

European Search Report for PCT/JP2012/054279 dated Mar. 11, 2016.

* cited by examiner

PARTICLE AGGREGATE, MANUFACTURING METHOD FOR PARTICLE AGGREGATE, FLUORESCENCE ENHANCING ELEMENT, AND DEVICE USING PHOTOCHEMICAL REACTIONS

CROSS REFERENCE TO RELATED APPLICATIONS

This application is a national phase of PCT/JP2012/054279 filed on Feb. 22, 2012 which claims priority to Japanese Patent Application 2011-036468 filed Feb. 22, 2011, the entire disclosures of which are incorporated by reference herein.

TECHNICAL FIELD

The present invention relates to a particle aggregate, a production method for a particle aggregate, a light enhancing element and an apparatus utilizing a photochemical reaction.

BACKGROUND ART

It has been known that a metal nanoparticle having a nanometer scale size has characters different from the metal in a bulky size. A metal nanoparticle has characters, for example, of melting point depression, quantum effect, specific surface area increase, and the like. It has been found recently that a new character is added by aggregating metal nanoparticles, and the related studies have been energetically carried out. For example, a large number of reports have appeared on applications of a metal nanoparticle aggregate, such as a photocatalytic reaction, a Raman enhancing element, a chemical formula sensor, and the like.

For example, in Non Patent Literature 1 is described that a 3-dimensional aggregate of zinc oxide fine particles enhanced light scattering and increased the photoelectric conversion efficiency in a solar cell. Further, in Non Patent Literature 2 is described that a 3-dimensional superlattice structure of gold nano-particles remarkably intensified a Raman scattering spectrum. Further, in Patent Literature 1 is described that by arraying regularly colloidal particles infrared light was reflected efficiently and the transmittance of visible light was increased. In Non Patent Literature 3 is described that colloidal fine particles encapsulating a drug were used as a drug delivery system.

While studies on a metal nanoparticle aggregate are progressing, several methods for aggregating metal nanoparticles have been found and reported.

For example Non Patent Literature 4 discloses a method for aggregating metal nanoparticles on a substrate provided with a polymer. Further, Non Patent Literature 5 discloses a method for aggregating metal nanoparticles using a template composed of silica particles.

CITATION LIST

Patent Literature

Patent Literature 1: Unexamined Japanese Patent Application Kokai Publication No. 2009-20437.

Non Patent Literature

Non Patent Literature 1: Qifeng Zhang, et al., Adv. Funct. Mater., 2008, 18, 1654-1660.

Non Patent Literature 2: E. S. Shibu, et al. Chem. Mater., 2009, 21, 3773-3781.

Non Patent Literature 3: D. Patra, et al., Chem. Asian J., 2010, 5, 2442-2453.

Non Patent Literature 4: Shouheng Sun, et al., J. Am. Chem. Soc., 2002, 124 (12), 2884-2885.

Non Patent Literature 5: Sang-Wook Kim, et al., J. Am. Chem. Soc., 2002, 124 (26), 7642-7643.

SUMMARY OF INVENTION

Technical Problem

The method for aggregating nanoparticles described in Non Patent Literature 4 is limited to aggregation on a planar substrate, and requires a plurality of processing steps, which makes the operation troublesome in some cases. While the method for aggregating nanoparticles described in Non Patent Literature 5 needs a template for aggregation, and further requires an operation for dissolving and removing the template by hydrogen fluoride after the aggregation of nanoparticles, which tends to make the operation troublesome.

The present invention was made under such circumstances, with an object to provide a particle aggregate, a light enhancing element and an apparatus utilizing a photochemical reaction, that is able to be produced by a simple operation and are superior in a light enhancing effect. Further, the present invention has an object to provide a production method for a particle aggregate that is able to be exercised by a simple operation.

Solution to Problem

For achieving the object, a particle aggregate according to the first aspect of the present invention is a hollow particle aggregate formed by aggregating a plurality of self-organizable particles, wherein a metal core is modified by a surface modifier for a metal core comprising a first segment comprising an optionally branched fluorinated alkylene glycol group, an optionally branched fluorinated alkylene group, or an optionally branched fluorinated azaalkylene group; a second segment comprising at least one hydrophilic group and bonding to one of the ends of a main chain of the first segment; and a functional group that bonds directly or indirectly to the another end of the main chain of the first segment and is able to bond to the metal core.

It is possible that the surface modifier for a metal core is expressed by a general formula $R_t-(R_h-O)_t-R_f-R_a-X$, [wherein $R_t$ represents a hydrogen atom, a hydroxy group, a C1 to C4 alkoxyl group, or a C1 to C4 alkyl group, $R_h$ represents an optionally branched C2 to C6 alkylene group, $R_f$ is selected from the set consisting of the following general formulas (1) and (2),

[Chem. Formula 1]

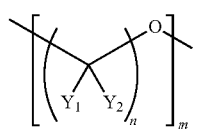

-continued

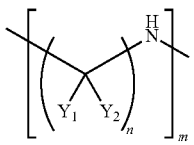
(2)

$R_a$ represents a C3 to C18 normal chain alkyl, a C3 to C18 branched alkyl or a C3 to C18 aralkyl, X represents a thiol group, a cyano group, a dithiol group, an amino group or an isocyano group, each of $Y_1$ and $Y_2$ represents a hydrogen atom or a fluorine atom, and at least one of $Y_1$ and $Y_2$ is a fluorine atom, l represents an integer of 1 to 12, m represents an integer of 1 to 12, n represents an integer of 1 to 6, and —$(R_h$—O$)_l$— includes a cyclic group].

It is possible that the hollow particle aggregate is a near-spherical body.

It is possible that the diameter of the near-spherical body is 30 to 400 nm.

It is possible that the coverage of a surface of the metal core by the surface modifier for a metal core is 20% or more.

It is possible that the metal core contains gold, platinum, silver, copper, iron or a semiconductor quantum dot.

A production method for a particle aggregate according to the second aspect of the present invention comprises a step for mixing in a solvent a metal core comprising a ligand on a surface, and a surface modifier for a metal core comprising a first segment comprising an optionally branched fluorinated alkylene glycol group, an optionally branched fluorinated alkylene group, or an optionally branched fluorinated azaalkylene group; a second segment comprising at least one hydrophilic group and bonding to one of the ends of a main chain of the first segment; and a functional group that bonds directly or indirectly to the another end of the main chain of the first segment and is able to bond to the metal core.

It is possible that the surface modifier for a metal core is expressed by a general formula $R_t$—$(R_h$—O$)_l$—$R_f$—$R_a$—X, [wherein $R_t$ represents a hydrogen atom, a hydroxy group, a C1 to C4 alkoxyl group, or a C1 to C4 alkyl group, $R_h$ represents an optionally branched C2 to C6 alkylene group, $R_f$ is selected from the set consisting of the following general formulas (1) and (2),

[Chem. Formula 2]

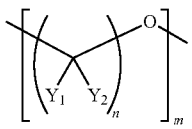
(1)

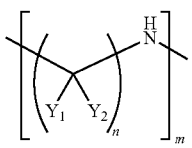
(2)

$R_a$ represents a C3 to C18 normal chain alkyl, a C3 to C18 branched alkyl or a C3 to C18 aralkyl, X represents a thiol group, a cyano group, a dithiol group, an amino group or an isocyano group, each of $Y_1$ and $Y_2$ represents a hydrogen atom or a fluorine atom, and at least one of $Y_1$ and $Y_2$ is a fluorine atom, l represents an integer of 1 to 12, m represents an integer of 1 to 12, n represents an integer of 1 to 6, and —$(R_h$—O$)_l$— includes a cyclic group].

It is possible that the production method for a particle aggregate comprises after the step further a step for replacing the solvent with a replacement solvent.

A light enhancing element according to the third aspect of the present invention comprises the hollow particle aggregate.

An apparatus utilizing a photochemical reaction according to the fourth aspect of the present invention comprises the light enhancing element.

Advantageous Effects of Invention

The present invention is able to provide a hollow particle aggregate producible with a simple operation and superior in light enhancing effect, a light enhancing element, and an apparatus utilizing a photochemical reaction. Further, the present invention is able to provide a production method for a hollow particle aggregate, which is able to be exercised by a simple operation.

DESCRIPTION OF EMBODIMENTS

Figure 1:
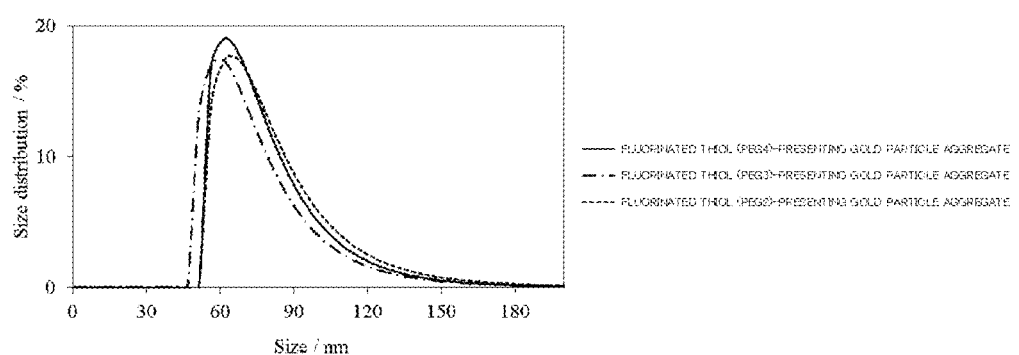
FIG. 1 is a graph showing the size distributions of particle aggregates in solutions according to an Example of the present invention.
Figure 2A:
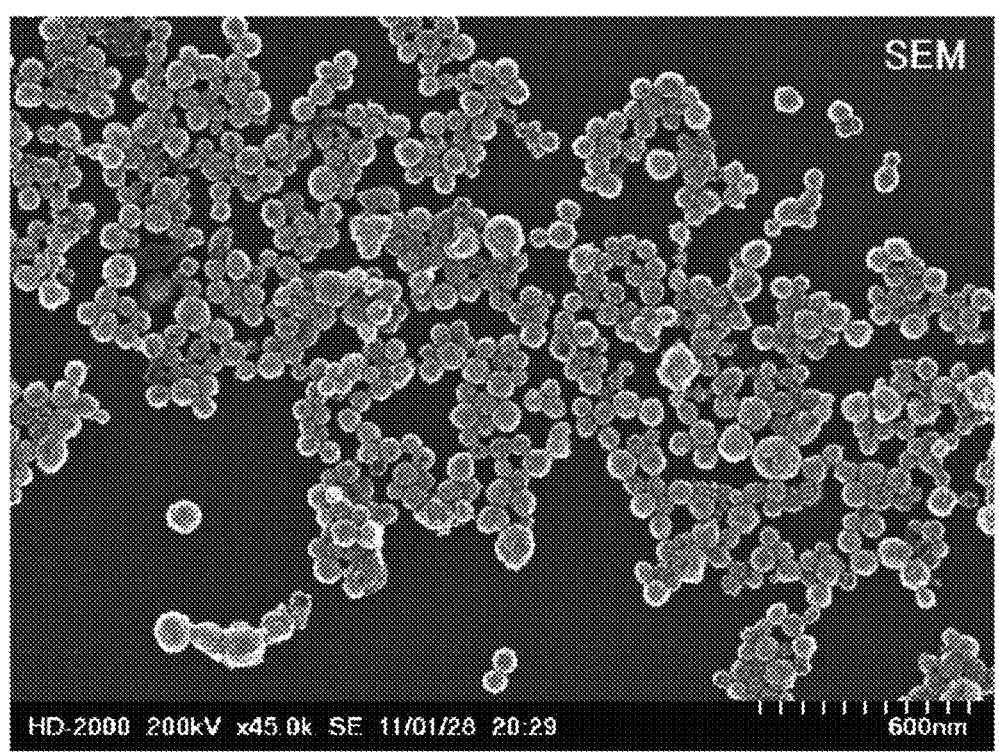
FIG. 2A is a picture showing an electron microscopic image (SEM image) of a plurality of particle aggregates according to an Example of the present invention.
Figure 2B:
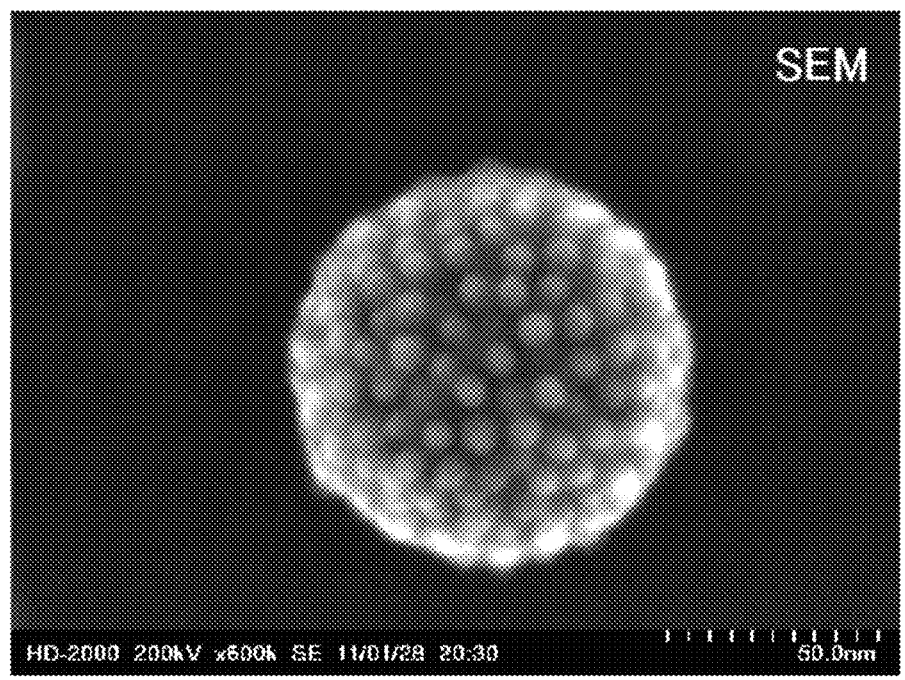
FIG. 2B is a picture showing an electron microscopic image (SEM image) of a single particle aggregate according to an Example of the present invention.
Figure 2C:
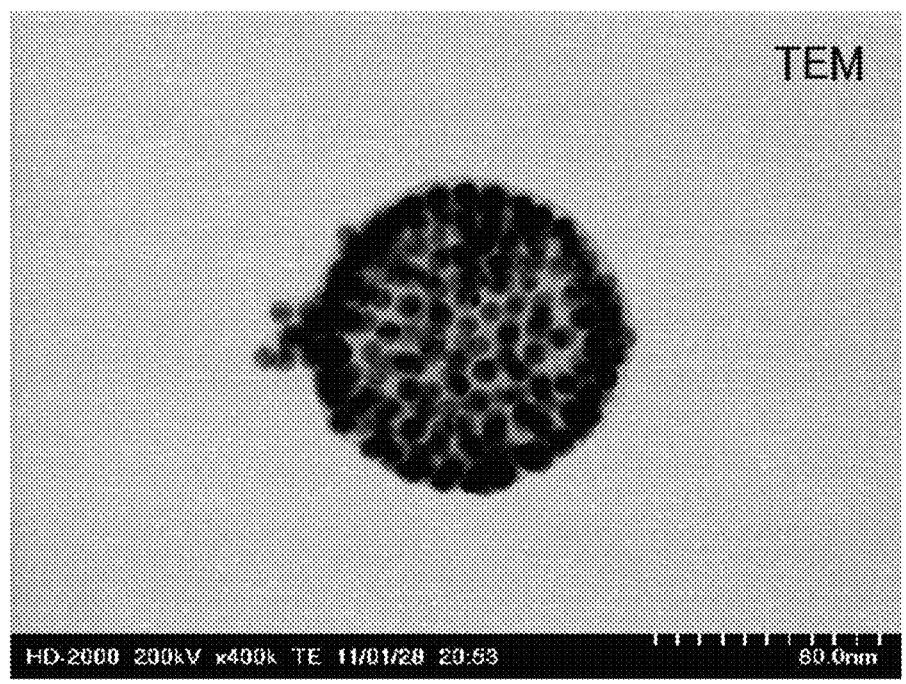
FIG. 2C is a picture showing an electron microscopic image (TEM image) of a single particle aggregate according to an Example of the present invention.
Figure 2D:
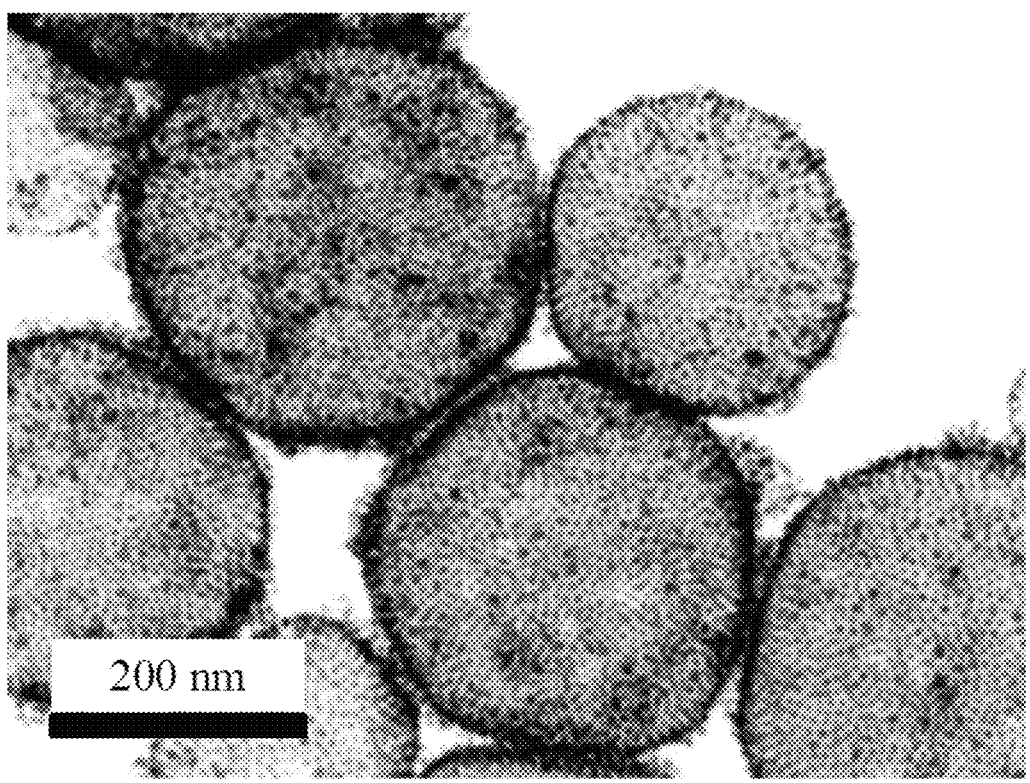
FIG. 2D is a picture showing an electron microscopic image (TEM image) of a plurality of particle aggregates according to an Example of the present invention.

Embodiments of the present invention will be described below in detail.

Firstly, a self-organizable particle and a surface modifier for a metal core according to the present invention will be described in detail.

A self-organizable particle according to the present invention is characterized in that a metal core is modified by a surface modifier for a metal core comprising a first segment comprising an optionally branched fluorinated alkylene glycol group, an optionally branched fluorinated alkylene group, or an optionally branched fluorinated azaalkylene group; a second segment comprising at least one hydrophilic group and bonding to one of the ends of a main chain of the first segment; and a functional group that bonds directly or indirectly to the another end of the main chain of the first segment and is able to bond to the metal core.

The metal core means a metal nanoparticle having a nanometer scale diameter.

As a composing element for a metal core, it is possible that gold, platinum, silver, copper, iron, semiconductor quantum dot, zinc oxide fine particle, titanium oxide fine particle, and the like, as well as a mixture thereof is used. For example, when gold, platinum, silver, or copper is used as a composing element for a metal core, an effect for enhancing the light absorption by localized surface plasmon resonance described below is promoted. As a composing element for a metal core, it is possible that an element is selected appropriately, insofar as the same exhibits an advantageous effect of the present invention.

The diameter of a metal core is approx. 1 to 200 nm, for example, 5 nm, 10 nm, 20 nm, 50 nm, 100 nm, 200 nm and the like. When the diameter of a metal core is, for example, 20 to 200 nm, the effect for enhancing the light absorption by localized surface plasmon resonance described below is promoted.

The first segment provided in a surface modifier for a metal core has an optionally branched fluorinated alkylene glycol group, an optionally branched fluorinated alkylene group, or an optionally branched fluorinated azaalkylene group.

Examples of a fluorinated alkylene glycol group include such groups as obtained by removing one of two hydroxy groups and removing a hydrogen atom of the other hydroxy group, being possessed by fluorinated tetraethylene glycol (FTEG), fluorinated triethylene glycol, fluorinated diethylene glycol, fluorinated monoethylene glycol, fluorinated propylene glycol, fluorinated. butylene glycol, and the like.

It is possible that the fluorinated alkylene glycol group is represented by the following general formula. In this case, each of $Y_1$ and $Y_2$ represents a hydrogen atom or a fluorine atom, and at least one of $Y_1$ and $Y_2$ is a fluorine atom, m represents an integer of 1 to 12, and n represents an integer of 1 to 6.

[Chem. Formula 3]

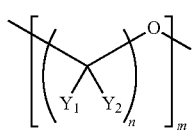

As the fluorinated alkylene glycol group, such groups as obtained by removing one of two hydroxy groups and removing a hydrogen atom of the other hydroxy group, being possessed by, for example, fluorinated tetraethylene glycol (FTEG), fluorinated triethylene glycol, or fluorinated diethylene glycol is favorably used, and a group obtained by removing one of two hydroxy groups and removing a hydrogen atom of the other hydroxy group, being possessed by, for example, fluorinated tetraethylene glycol (FTEG) is able to be more favorably used.

Examples of the fluorinated alkylene group include a group obtained by substituting a fluorine atom for a part or all of hydrogen atoms of a C2 to C12 alkylene group. It is possible that the fluorinated alkylene group has, for example, an ether bond. Examples of a fluorinated alkylene group having an ether bond include such groups as obtained by removing one of two hydroxy groups and removing a hydrogen atom of the other hydroxy group, being possessed by 1H,1H,4H,4H-perfluoro-1,4-butanediol; 1H,1H,5H,5H-perfluoro-1,5-pentanediol; 1H,1H,6H,6H-perfluoro-1,6-hexanediol; 1H,1H,8H,8H-perfluoro-1,8-octanediol; 1H,1H,9H,9H-perfluoro-1,9-nonanediol; 1H,1H,10H,10H-perfluoro-1,10-decanediol; and 1H,1H,12H,12H-perfluoro-1,12-dodecanediol.

Examples of the fluorinated azaalkylene group include a group obtained by substituting a fluorine atom for a part or all of hydrogen atoms of a C2 to C12 azaalkylene group. For example, —$CH_2$—$CF_2$—NH—, —$CF_2$—$CF_2$—NH—, —$CF_2$—$CH_2$—NH—, —$CH_2$—$CF_2$—NH—$CF_2$—$CH_2$—NH—, —$CF_2$—$CF_2$—NH—$CF_2$—$CH_2$—NH—, and —$CH_2$—$CF_2$—NH—$CH_2$—$CF_2$—NH— are used.

It is possible that the fluorinated azaalkylene group is represented by the following general formula. In this case, each of $Y_1$ and $Y_2$ represents a hydrogen atom or a fluorine atom, and at least one of $Y_1$ and $Y_2$ is a fluorine atom, m represents an integer of 1 to 12, and n represents an integer of 1 to 6.

[Chem. Formula 4]

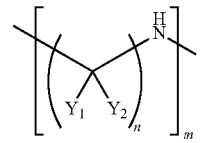

As an optionally branched fluorinated alkylene glycol group, an optionally branched fluorinated alkylene group, or an optionally branched fluorinated azaalkylene group, contained in the first segment, it is possible that any group is selected appropriately, insofar as the same exhibits an advantageous effect of the present invention.

If the first segment contains an optionally branched fluorinated alkylene glycol group, an optionally branched fluorinated alkylene group, or an optionally branched fluorinated azaalkylene group, it is able to have a character with high affinity to a hydrophobic organic solvent but low affinity to water.

The second segment provided in a surface modifier for a metal core has at least one hydrophilic group. The second segment has as a hydrophilic group, for example, a hydroxy group, and an ether group. Examples of the ether group include a group obtained by removing a hydrogen atom from one of two hydroxy groups, being possessed by tetraethylene glycol (PEG4), triethylene glycol (PEG3), diethylene glycol (PEG2), ethylene glycol, pentaethyne glycol, hexaethylene glycol, nonaethylene glycol, heptaethylene glycol, decaethylene glycol, and dodecaethylene glycol. Further, It is possible that, as the ether group, for example, a group containing 12-crown 4-ether, 15-crown 5-ether, 18-crown 6-ether, and the like, are used.

It is possible that the second segment is represented by the general formula $R_t$—$(R_h$—$O)_l$—. In this case, $R_t$ represents a hydrogen atom, a hydroxy group, a C1 to C4 alkoxyl group or a C1 to C4 alkyl group, $R_h$ represents an optionally branched C2 to C6 alkylene group, l represents an integer of 1 to 12, and —$(R_h$—$O)_l$— includes a cyclic group. The alkoxyl group includes, for example, a methoxy group, and an ethoxy group.

As the second segment, for example, such groups as obtained by removing a hydrogen atom from one of two hydroxy groups, being possessed by, for example, PEG4, PEG3, PEG2, ethylene glycol, pentaethylene glycol, hexaethylene glycol, nonaethylene glycol, heptaethylene glycol, decaethylene glycol, and dodecaethylene glycol, and the like, are favorably used, and, for example, a group obtained by removing a hydrogen atom from one of two hydroxy groups being possessed by, for example, PEG4, PEG3 or PEG2 is able to be more favorably used. As a hydrophilic group contained in the second segment, It is possible that any group is selected appropriately, insofar as the same exhibits an advantageous effect of the present invention.

If the second segment has at least one hydrophilic group, the second segment is able to have a character with low affinity to a hydrophobic organic solvent but high affinity to water.

The second segment bonds, for example, covalently to an end of a main chain of the first segment.

A functional group contained in a surface modifier for a metal core is a functional group that is able to bond to a metal core. Any functional group that is able to bond to a metal core is able to be used, and example of the functional group include a thiol group, a cyano group, a dithiol group, an amino group and an isocyano group, and, for example, a thiol group is able to be used favorably. As the functional group, it is possible that any group is selected appropriately, insofar as the same exhibits an advantageous effect of the present invention.

A functional group contained in a surface modifier for a metal core bonds directly or indirectly to the end opposite to the end of a main chain of the first segment, which is bonded with the second segment.

The case that a functional group bonds directly to the opposite end of a main chain of the first segment means a case that a functional group bonds, for example, covalently to the opposite end of a main chain of the first segment.

The case that a functional group bonds indirectly to another end of a main chain of the first segment means a case that a functional group bonds to the first segment, for example, through a third segment bonded to another end of a main chain of the first segment. As the third segment, for example, C3 to C18 normal chain alkyl, C3 to C18 branched alkyl, or C3 to C18 aralkyl is used. In this case, a functional group bonds, for example, covalently to the end of a main chain of the third segment opposite to the end bonded with the first segment.

A surface modifier for a metal core contains, as above, the first segment, the second segment, and the functional group.

It is possible that the surface modifier for a metal core is represent by the general formula $R_t\text{—}(R_h\text{—}O)_l\text{—}R_f\text{—}R_a\text{—}X$, wherein $R_t$ represents a hydrogen atom, a hydroxy group, a C1 to C4 alkoxyl group or a C1 to C4 alkyl group, $R_h$ represents an optionally branched C2 to C6 alkylene group, and $R_f$ is selected from the set consisting of the following general formulas (1) and (2),

[Chem. Formula 5]

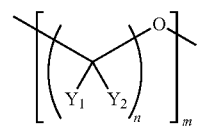

(1)

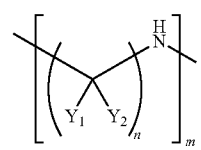

(2)

$R_a$ represents C3 to C18 normal chain alkyl, C3 to C18 branched alkyl or C3 to C18 aralkyl, X represents a thiol group, a cyano group, a dithiol group, an amino group or an isocyano group, each of $Y_1$ and $Y_2$ represents a hydrogen atom or a fluorine atom, and at least one of $Y_1$ and $Y_2$ is a fluorine atom, l represents an integer of 1 to 12, m represents an integer of 1 to 12, n represents an integer of 1 to 6, and —$(R_h\text{—}O)_l$— includes a cyclic group.

If the surface modifier for a metal core is represented by the general formula $R_t\text{—}(R_h\text{—}O)_l\text{—}R_f\text{—}R_a\text{—}X$, in the formula $R_t\text{—}(R_h\text{—}O)_l\text{—}$ represents the second segment, $R_f$ represents the first segment, $R_a$ represents the third segment, and X represents a functional group.

As the surface modifier for a metal core, for example, 14,14,16,16,17,17,19,19,20,20,22,22-dodecafluoro-35-mercapto-3,6,9,12,15,18,21,24-octaoxapentatriacontan-1-ol (PEG4-FTEG-C11-SH), 11,11,13,13,14,14,16,16,17,17,19,19-dodecafluoro-32-mercapto-3,6,9,12,15,18,21-heptaoxadotriacontan-1-ol (PEG3-FTEG-C11-SH), and 8,8,10,10,11,11,13,13,14,14,16,16-dodecafluoro-29-mercapto-3,6,9,12,15,18-hexaoxanonacosan-1-ol (PEG2-FTEG-C11-SH) is able to be favorably used. It is possible that the first segment is referred to herein occasionally as "a fluorinated segment", and the second segment as "a PEG segment". The structures of the respective compounds are as the following chemical formulas:

[Chem. Formula 6]

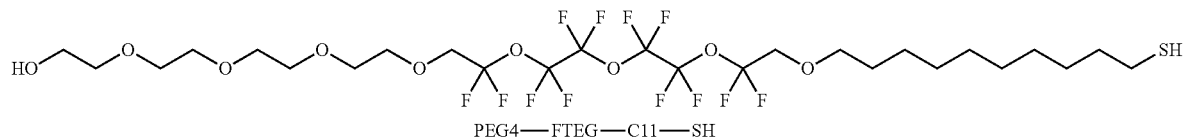

PEG4—FTEG—C11—SH

[Chem. Formula 7]

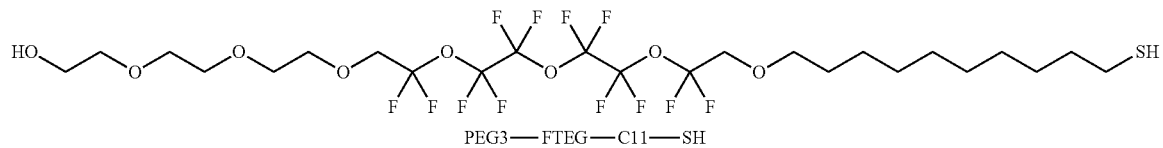

PEG3—FTEG—C11—SH

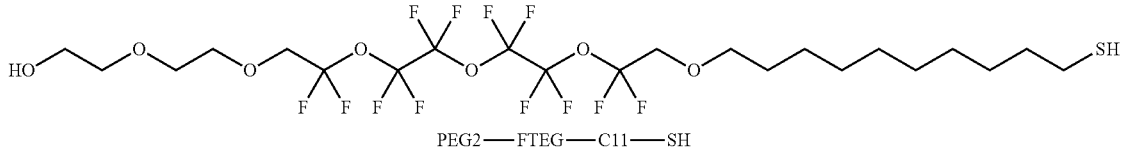

PEG2——FTEG——C11——SH

A self-organizable particle according to the present invention is characterized in that a metal core is modified with the surface modifier for a metal core. In this connection, modification means a state that a functional group contained in a surface modifier for a metal core bonds, for example, through a coordinate bond to a metal core, so as to bind the surface modifier for a metal core and the metal core. In this case, the coverage of a surface modifier on a metal core surface (Number of metal atoms bonded by surface modifier/Number of metal atoms exposed to metal core surface X 100) of 20% or more is acceptable, if a metal core is, for example, a gold nanoparticle with the diameter of 5 nm, and, for example, approx. 50 to 60% is preferable.

The coverage by a surface modifier on a metal core surface is able to be measured by an ICP emission analyzer (for example, ICPE-9000 (by Shimadzu Corporation)). For example, if gold is used as a composing element for a metal core, and PEG4-FTEG-C11-SH, PEG3-FTEG-C11-SH, or PEG2-FTEG-C11-SH, is used as a surface modifier, an obtained hollow particle aggregate (described below) is dissolved in aqua regia, and burnt in high-frequency inductively coupled plasma to determine the content ratio of gold atom to sulfur atom, and the coverage is able to be calculated therefrom.

Examples of the self-organizable particle according to the present invention include a fluorinated thiol-presenting gold particle, in which a metal core composed of a gold nanoparticle is coated by a surface modifier for a metal core PEG4-FTEG-C11-SH that contains a first segment composed of a group obtained by removing one of two hydroxy groups and removing a hydrogen atom of the other hydroxy group being possessed by FTEG, a second segment composed of a group obtained by removing a hydrogen atom from one of two hydroxy groups, being possessed by PEG4, a functional group composed of a thiol group, and a third domain composed of a C11 alkyl chain. The fluorinated thiol-presenting gold particle is able to be expressed as follows:

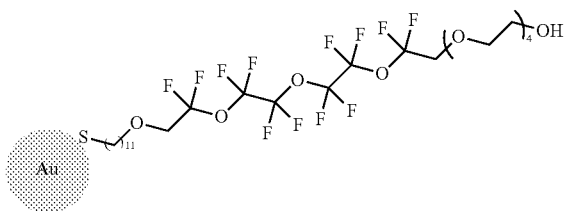

Fluorinated Thiol-Presenting Gold Particle

Next, a particle aggregate according to the present invention will be described in detail.

A particle aggregate according to the present invention is a hollow particle aggregate formed by aggregating a plurality of self-organizable particles described above. The self-organizable particles are aggregated 3-dimensionally. A hollow particle aggregate according to the present invention is formed by aggregating, for example, approx. 100 to 200 self-organizable particles mentioned above.

Since there is an empty space inside a hollow particle aggregate according to the present invention, the dispersibility of the hollow particle aggregate in a solvent is able to be improved. Further, by encapsulation of a drug and the like in an internal space of a hollow particle aggregate, a hollow particle aggregate is able to be applied to an in vivo diagnostic agent, a drug delivery system, and the like.

The fact that a hollow particle aggregate according to the present invention is a hollow body is able to be confirmed, for example, by seeing through the inside of a hollow particle aggregate by observation using an electron microscope (TEM image). It is able to also be confirmed by comparing found values of X-ray scattering intensity in an X-ray small-angle scattering (SAXS) analysis for a hollow particle aggregate and values from a core-shell model, to investigate whether the respective SAXS scattering profiles coincide or not. It is possible that any confirmation method is selected appropriately, insofar as the same exhibits an advantageous effect of the present invention.

It is possible that a hollow particle aggregate according to the present invention is formed in shapes of, for example, a near-spherical body, a near-spheroid body, a dome, a flat plate and the like, and preferably formed in a shape of a near-spherical body.

The shape of a hollow particle aggregate according to the present invention (a near-spherical body and the like) is able to be confirmed by observation with an electron microscope (SEM image or TEM image). It is possible that any confirmation method on the shape is selected appropriately, insofar as the same exhibits an advantageous effect of the present invention.

In the case a hollow particle aggregate according to the present invention is a near-spherical body, the diameter thereof is 30 to 400 nm. Although the diameter is able to be adjusted appropriately according to an end use, 30 to 200 nm is generally preferable. For example, if used for a light enhancing element and a light sensing material as described below, the diameter is preferably 50 to 200 nm and more preferably 80 to 120 nm from a viewpoint of light enhancement. Further, if used for a drug delivery system as described below, the diameter is preferably 30 to 200 nm and more preferably 50 to 100 nm from a viewpoint of delivery efficiency. While, the average diameter of a hollow particle aggregate (near-spherical body) is approx. 60 nm, so long as the diameter distributes, for example, also in a range of 70 to 80 nm.

The diameter of a hollow particle aggregate (near-spherical body) according to the present invention is able to be measured by observation with an electron microscope (SEM image or TEM image). It is possible that any measuring method is selected appropriately, insofar as the same exhibits an advantageous effect of the present invention.

With respect to a hollow particle aggregate (near-spherical body) according to the present invention, a plurality of self-organizable particles are arrayed, for example, in a 1-layer structure or 2-layer structure, preferably in a 1-layer structure on a near-spherical body surface, and inside the spherical body there exists a spherical empty space. In this case, the inner diameter of the spherical space inside the spherical body is able to be, for example, approx. 50 to 60 nm.

Hollow particle aggregates according to the present invention is able to be spread over a solid substrate, for example, by a drop casting process. A hollow particle aggregate according to the present invention is able to maintain stably the shape in which a hollow particle aggregate is formed even in a dry state as in the case having been spread over a solid substrate.

A hollow particle aggregate according to the present invention is able to be present in the state dispersed stably and homogeneously in a polymer, for example, even under the condition that the same is embedded in a polymer. Examples of the polymer to be used include an epoxy resin, agarose gel, a methacrylate resin, and isopropylacrylamide. It is possible that any polymer is selected appropriately, insofar as the same exhibits an advantageous effect of the present invention. As for a method for embedding a hollow particle aggregate in a polymer, for example, a method of mixing a hollow particle aggregate and a polymer, and thermally curing or photo-curing the mixture is usable, but It is possible that any embedding method is selected appropriately, insofar as the same exhibits an advantageous effect of the present invention.

Next, a production method for a particle aggregate according to the present invention will be described in detail.

A production method for a particle aggregate according to the present invention includes a step for mixing a metal core having a ligand on a surface and the surface modifier for a metal core in a solvent (hereinafter referred to as "a mixing step").

Examples of a ligand that a metal core possesses on a surface include an organic acid, such as citric acid, ascorbic acid, and tannic acid, polyvinylpyrrolidone, polyvinyl alcohol, and cetyltrimethylammonium bromide. If a metal core possessing citric acid, ascorbic acid, and tannic acid as a ligand on a surface, a ligand exchange reaction and self organization described below is able to be progressed more smoothly.

Examples of a composing material for a metal core include gold, platinum, silver, copper, iron, semiconductor quantum dot, zinc oxide fine particles, and titanium oxide fine particles.

As a metal core possessing a ligand on a surface, It is possible that, for example, a commercially available gold-citric acid colloidal solution and the like is used.

In the mixing step by mixing a metal core possessing a ligand on a surface and a surface modifier for a metal core in a solvent, a functional group contained in the surface modifier for a metal core is able to be bonded to a surface of the metal core, for example, through a coordinate bond. By mixing a metal core possessing a ligand on a surface and a surface modifier in a solvent, for example, a reaction for exchanging a ligand present on a surface of the metal core with a functional group contained in a surface modifier (hereinafter referred to as "a ligand exchange reaction") occurs. A self-organizable particle according to the present invention is able to be thus obtained.

Self organization of particles occurs in the mixing step. Self organization means herein that organization and aggregation of particles take place according to a natural order without inducement or control from the outside. Self organization of particles progresses in parallel with the ligand exchange reaction. A particle aggregate according to the present invention is formed by self organization of particles. By self organization, for example, hollow particle aggregates with uniform diameters is able to be obtained.

It is believed that the balance between the affinity to a hydrophobic organic solvent of the first segment and the non-affinity to a hydrophobic organic solvent of the second segment contained in a surface modifier for a metal core contributes to self organization in the mixing step. It is also believed that self organization occurs spontaneously by a repulsive action between the second segments in a solvent. Further, for example, by using a surface modifier containing the third segment, the third segment acts as a spacer between the metal core and the first segment, which occasionally promotes self organization.

In the mixing step as a solvent, for example, a solvent having an ether bond, a solvent having a SP value of approx. 8 to 10 (cal/mL) or the like, or a mixture thereof is used. The SP value herein is a value representing a solubility parameter by Hildebrand, et al., which is cohesive energy density (evaporation energy of a molecule per unit area) raised to the ½ power and represents the magnitude of polarity per unit volume.

Examples of a solvent having an ether bond include tetrahydrofuran (THF), dimethyl ether, diethyl ether, diisopropyl ether, di-n-butyl ether, methyl-tert-butyl ether, anisole, 1,4-dioxane, 1,2-dimethoxyethane, bis(2-methoxyethyl)ether, tetrahydropyran and a mixture thereof.

Examples of a solvent with a SP value of approx. 8 to 10 (cal/mL) to be used include cyclohexane, carbon tetrachloride, xylene, ethyl acetate, toluene, benzene, chloroform, trichloroethylene, methyl ethyl ketone, acetone, and a mixture thereof.

As a solvent to be used in the mixing step, for example, a solvent having an ether bond is able to be used favorably, and for example, THF is able to be more favorably used.

As a solvent to be used in the mixing step, it is possible that any solvent is selected appropriately, insofar as the same exhibits an advantageous effect of the present invention.

The mixing ratio of a metal core to a surface modifier in the mixing step is preferably, for example, metal core: surface modifier=1:100,000 to 1:500,000 (by mol). In the range of a mixing ratio, the ligand exchange reaction and self organization is able to be progressed more smoothly.

When a metal core having a ligand on a surface and a surface modifier are mixed in a solvent in the mixing step, it is possible that stirring is performed. By doing so, the ligand exchange reaction and self organization is able to be progressed more smoothly. Further, for mixing a metal core having a ligand on a surface and a surface modifier are mixed in a solvent, it is possible that an ultrasonic treatment is conducted. By conducting an ultrasonic treatment, the solubility of a metal core having a ligand on a surface in a solvent is able to be improved, so as to promote progress of the ligand exchange reaction and self organization.

In the mixing step as a surface modifier for a metal core it is possible that a mixture of different types of surface modifiers is used.

A particle aggregate is able to be yielded in the mixing step. It is possible that the particle aggregate yielded in the step contain a self-organizable particle. If, for example, the ligand exchange reaction and self organization have progressed well in the mixing step, a larger amount of the particle aggregate is able to be yielded.

It is possible that a production method for a particle aggregate according to the present invention further includes after the mixing step, for example, a step for centrifuging a mixture liquid of a metal core having a ligand on a surface and a surface modifier, removing a supernatant, adding a solvent to a pellet followed by stirring and an ultrasonic treatment, centrifuging again the mixture, and removing a supernatant (hereinafter referred to as "a reslurry step"). By conducting the reslurry step, a contaminant in the mixture liquid is removed and it is possible that self organization is progressed occasionally more smoothly. By doing so, a larger amount of a particle aggregate is able to be produced. As a solvent to be used in the reslurry step, it is possible that a similar solvent as used in the mixing step is used.

It is possible that a series or operations in the mixing step are carried out simply by mixing a metal core having a ligand on a surface and a surface modifier in a solvent. Thus, a production method for a particle aggregate according to the present invention is able to be carried out by a simple operation.

While, formation of a particle aggregate is able to be confirmed by observing whether the measured absorbance of a reaction solution after the mixing step has shifted to the long-wavelength side compared to the absorbance of a reaction solution before the mixing step or a solution having not formed a particle aggregate. Further, formation of a particle aggregate is able to be also confirmed by observing the color change of a reaction solution. The color of a reaction solution changes, for example, from red to purple, from before to after the mixing step.

It is possible that a production method for a particle aggregate according to the present invention includes after the mixing step or the reslurry step further a step for replacing a solvent with a replacement solvent. As a replacement solvent, it is possible that a solvent similar to those used in the mixing step or the reslurry step is used, or it is possible that a solvent different from those used in the mixing step or the reslurry step is also used. Examples of a replacement solvent to be used include THF, ethyl acetate, dichloromethane, butanol, methanol, acetone, and dimethylformamide (DMF). A particle aggregate according to the present invention is able to maintain stably in a replacement solvent such a condition, into which the particle aggregate was formed. If a particle aggregate according to the present invention is formed in the mixing step or the reslurry step in a solvent and then the solvent is replaced with a replacement solvent, the particle aggregate is able to maintain stably in a replacement solvent such a condition, into which the particle aggregate was formed.

An example of a ligand exchange reaction and self organization in the mixing step is shown below. In the example, as a metal core having a ligand on a surface is used a gold-citric acid colloidal solution, and as a surface modifier for a metal core is used PEG4-FTEG-C11-SH.

[Chem. Formula 10]

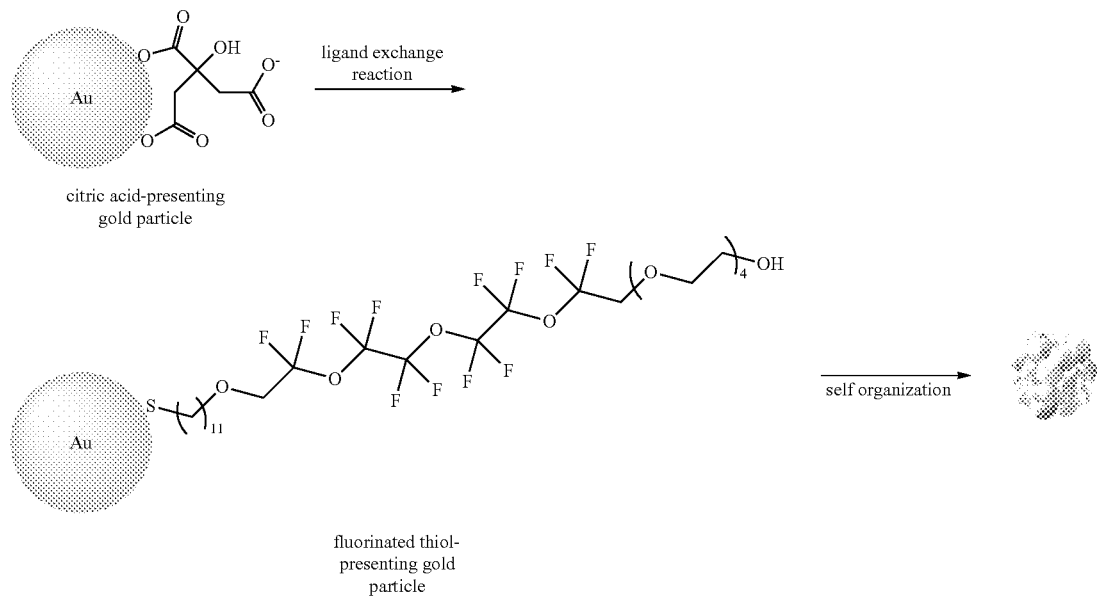

Next, a light enhancing element according to the present invention will be described in detail.

A light enhancing element according to the present invention contains the hollow particle aggregate.

A light enhancing element means herein an element that enhances the light absorption by localized surface plasmon resonance. The light absorption by localized surface plasmon resonance means that a particle and a particle aggregate absorb light with a specific wavelength and light energy or an electric field caused therefrom accumulates on a particle and a particle aggregate. The light absorption by localized surface plasmon resonance is able to occur with a particle, but if a plurality of particles aggregate to an aggregate, it is possible that the absorption is sometimes enhanced. This is because when particles aggregate to form an aggregate, gaps are formed among particles and light accumulates to the gaps. As a method for confirming light absorption by localized surface plasmon resonance, for example, a Raman spectroscopy method is able to be used. For a Raman spectroscopy method, by utilizing electric field enhancement by localized surface plasmon resonance, a Raman spectrum is able to be measured easier.

A light enhancing element according to the present invention includes, for example, a photoreaction catalyst. Since the photoreaction catalyst contains a hollow particle aggregate according to the present invention, light is able to be accumulated. Owing to the energy thereof, for example, a chemical reaction is able to be progressed.

A light enhancing element according to the present invention includes, for example, an in vivo diagnostic agent. In this case, a drug or the like that is able to be visualized by a light enhancing effect is first, for example, encapsulated in an internal space of a hollow particle aggregate. Next, such hollow particle aggregates encapsulating the drug are administered to a patient, and when the hollow particle aggregates gather at an affected region (for example, cancer tissue), the aggregates are irradiated with light from outside the body. Since a drug encapsulated in a hollow particle aggregate is able to be visualized by the light enhancing effect, the affected region of the patient is able to be diagnosed.

A light enhancing element according to the present invention includes, for example, a drug delivery system. In this case, first, for example, a drug or the like is encapsulated in an internal space of a hollow particle aggregate. Next, such hollow particle aggregates encapsulating the drug are administered to a patient, and when the hollow particle aggregates gather at an affected region (for example, cancer tissue), the hollow particle aggregates are regulated to be disintegrated. By doing so, the drug is able to be released from the inside of the hollow particle aggregates to cure the affected region.

Generally, the diameter of a vehicle used in a drug delivery system is preferably 100 nm or less especially from a viewpoint of delivery efficiency when cancer tissues are targeted. Since the diameter of a hollow particle aggregate (near-spherical body) according to the present invention is able to be made 50 to 100 nm, a drug delivery system with higher delivery efficiency is able to be provided.

If a drug or the like is contained in the inside of a hollow particle aggregate according to the present invention, a higher Raman active scattering enhancement effect is able to be obtained. Therefore, if a hollow particle aggregate contains, for example, an anticancer agent (it is possible that the hollow particle aggregate contains additionally a Raman probe), the detection sensitivity of cancer tissues is able to be improved, and at the same time the anticancer agent is able to be released to cancer tissues as a target site from the inside of a hollow particle aggregate. As described above, with a hollow particle aggregate according to the present invention an affected region is able to be simultaneously diagnosed and cured.

It is possible that an inclusion in a light enhancing element according to the present invention is selected appropriately, insofar as the same exhibits an advantageous effect of the present invention.

Next, an apparatus utilizing a photochemical reaction according to the present invention will be described in detail.

An apparatus utilizing a photochemical reaction according to the present invention is provided with the light enhancing element. The apparatus includes, for example, a light sensing device, a light sensing material, a solar cell, and the like.

Since a light sensing device according to the present invention is provided with the light enhancing element, light is able to be accumulated. Therefore the light sensing device is able to conduct sensing with high sensitivity. Further, using, for example, a drug or the like encapsulated in an internal space of a hollow particle aggregate as a probe, sensing is able to be conducted.

A light sensing material according to the present invention contains the light enhancing element. A light enhancing element has a character to change the color due to a change in distance among particles. Therefore, for example, by mixing (embedding) a light sensing material according to the present invention in a polymer, the expansion and contraction, strain, or the like of a polymer caused by a temperature change, a humidity change and the like, is able to be detected by a color change. Since a light sensing material according to the present invention is able to be present in the state dispersed stably and homogeneously in a polymer as described above, it is particularly useful.

Since a solar cell according to the present invention includes the light enhancing element, sunlight is able to be accumulated. Therefore, the solar cell is able to convert efficiently light energy to electric power.

It is possible that an element to be included in an apparatus utilizing a photochemical reaction according to the present invention is selected appropriately, insofar as the same exhibits an advantageous effect of the present invention.

Example 1

The present invention will be specifically described below referring to Examples, provided that Examples are not intended to limit the scope of the present invention.

Syntheses of PEG4-FTEG-C11-SH,
PEG3-FTEG-C11-SH, and PEG2-FTEG-C11-S as
Surface Modifiers for a Metal Core (A) Synthesis of 10-undecene-1-tosylate (C11-OTs)

C11-OTs was synthesized as follows:

[Chem. Formula 11]

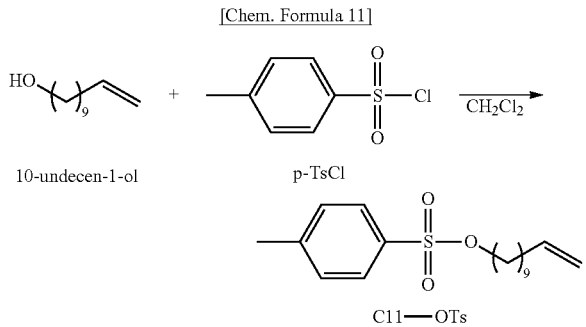

In a 300 mL-Erlenmeyer flask, 5.0 g (29.4 mmol) of 10-undecen-1-ol was dissolved in 20 mL of dichloromethane. After cooling the solution to 0° C., a solution of 8.14 mL (58.8 mmol) of triethylamine, 6.73 g (35.3 mmol) of p-toluenesulfonyl chloride (p-TsCl), and 0.56 g (58.8 mmol) of trimethylammonium chloride ($Me_3N\cdot HCl$) dissolved in 10 mL of dichloromethane was dropped with stirring. The mixture liquid was stirred at room temperature for 2 hours, then 10 mL of chloroform was added for dilution. The mixture was washed twice with approx. 10 mL of a saturated saline solution, and the organic layer was dried over sodium sulfate and concentrated under a reduced pressure. After purification by silica gel column chromatography (development: hexane→hexane:chloroform=1:1), transparent liquid C11-OTs (7.49 g, 23.23 mmol, 79%) was obtained. For the obtained compound the $^1$H-NMR spectrum data (600 MHz, CDCl$_3$) were δ/ppm=1.21-1.37 (br, 12H, alkyl chain), 1.59-1.65 (br, 2H, alkyl chain), 2.03 (q, 2H, J=7.44 Hz, =CH—CH$_2$—CH$_2$), 2.45 (s, 3H, CH$_3$ methyl), 4.01 (t, 2H, J=13.08, —CH$_2$—O—), 4.92-5.01 (br, 2H, olefin), 5.76-5.84 (br, 1H, olefin), 7.34 (d, 2H, J=8.22 Hz, phenyl), 7.79 (d, 2H, J=8.22 Hz, phenyl).

(B) Syntheses of 2-(2-(2-(2-hydroxyethoxy)ethoxy)ethoxy)ethyl 4-methylbenzenesulfonate (PEG4-OTs), 2-(2-(2-hydroxyethoxy)ethoxy)ethyl 4-methylbenzenesulfonate (PEG3-OTs), and 2-(2-hydroxyethoxy)ethyl 4-methylbenzenesulfonate (PEG2-OTs)

PEG4-OTs, PEG3-OTs, and PEG2-OTs were synthesized as follows.

[Chem. Formula 12]

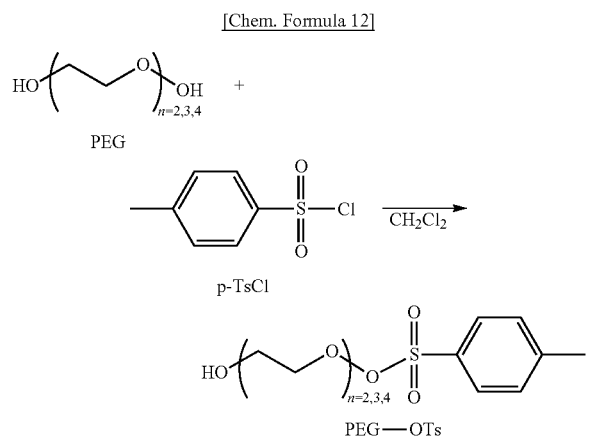

In a 300 mL-flask 10 g (51.5 mmol) of tetraethylene glycol was dissolved in 20 mL of dichloromethane. After the solution was cooled to 0° C., a solution of 7.12 mL (51.5 mmol) of triethylamine (Et$_3$N), 9.82 g (51.5 mmol) of p-toluenesulfonyl chloride (p-TsCl), and 0.98 g (10.3 mmol) of trimethylammonium chloride (Me$_3$N.HCl) dissolved in 30 mL of dichloromethane was dropped with stirring. The mixture liquid was stirred at room temperature for 2 hours, then 10 mL of chloroform was added for dilution. The mixture was washed twice with approx. 10 mL of a saturated saline solution, and the organic layer was dried over sodium sulfate and concentrated under a reduced pressure. After purification by silica gel column chromatography (development: chloroform), yellow liquid PEG4-OTs (10.05 g, 23.0 mmol, 45%) was obtained. For the obtained compound the $^1$H-NMR spectrum data (400 MHz, CDCl$_3$) were δ/ppm=2.44 (s, 3H, methyl), 3.56-3.70 (br, 14H, —CH$_2$—O—), 4.15 (t, 2H, J=9.48 Hz, —CH$_2$—O—S), 7.34 (d, 2H, J=8.21 Hz, phenyl), 7.79 (d, 2H, J=8.21 Hz, phenyl).

By syntheses same as above, except that triethylene glycol, and diethylene glycol were used instead of tetraethylene glycol, PEG3-OTs (7.94 g, 26.1 mmol, 39%) and PEG2-OTs (9.71 g, 36.9 mmol, 32%) were obtained. For the obtained PEG3-OTs the $^1$H-NMR spectrum data (400 MHz, CDCl$_3$) were δ/ppm=2.44 (s, 3H, methyl), 3.53-3.58 (br, 6H, —CH$_2$—O—), 3.68 (t, 4H, J=9.2 Hz, —CH$_2$—O—), 4.16 (t, 2H, J=8.68 Hz, —CH$_2$—O—S), 7.35 (d, 2H, J=7.32 Hz, phenyl), 7.79 (d, 2H, J=7.32 Hz, phenyl); and the result of MALDI-TOF MS analysis (m/z) was [M+H] calcd for C$_{13}$H$_{21}$O$_6$S, 305.36. Found, 305.2, [M+Na] calcd for C$_{13}$H$_{20}$O$_6$SNa, 327.35. Found, 327.20, [M+K] calcd for C$_{13}$H$_{20}$O$_6$K, 343.46. Found, 343.1. For the obtained PEG2-OTs the $^1$H-NMR spectrum data (400 MHz, CDCl$_3$) were δ/ppm=2.45 (s, 3H, methyl), 3.54-3.71 (br, 6H, —CH$_2$—O—), 4.20 (t, 2H, J=8.60 Hz, —CH$_2$—O—S), 7.35 (d, 2H, J=7.66 Hz, phenyl), 7.80 (d, 2H, J=7.66 Hz, phenyl); and the result of MALDI-TOF MS analysis (m/z) was [M+H] calcd for C$_{11}$H$_{17}$O$_5$S, 261.31. Found, 261.5, [M+Na] calcd for C$_{11}$H$_{16}$O$_5$SNa, 283.3. Found, 283.6.

(C) Synthesis of 2,2,4,4,5,5,7,7,8,8,10,10-dodecafluoro-3,6,9,12-tetraoxatricos-22-en-1-ol (FTEG-C11)

FTEG-C11 was synthesized as follows:

[Chem. Formula 13]

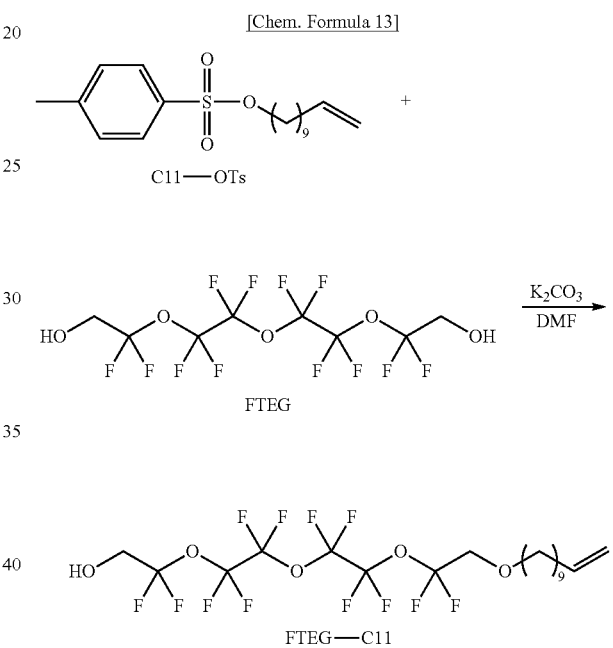

In a 300 mL-Nasu flask 7.59 g (18.5 mmol) of fluorinated tetraethylene glycol (FTEG) and 7.59 g (13.9 mmol) of potassium carbonate were dissolved in 5 mL of N,N-dimethylformamide (DMF). To this, the solution of 3.0 g (9.25 mmol) of C11-OTs obtained as above dissolved in 3 mL of DMF was dropped with stirring, and the mixture was further stirred at 80° C. in a nitrogen atmosphere for 14 hours. After evaporating the solvent by a rotary evaporator, the residue was diluted by adding 30 mL of ethyl acetate, and washed with 20 mL of a 15 weight-% aqueous solution of ammonium chloride. The organic layer was dried over sodium sulfate and concentrated under a reduced pressure. After purification by silica gel column chromatography (development: chloroform:hexane=1:2), transparent liquid FTEG-C11 (3.39 g, 6.02 mmol, 64%) was obtained. For the obtained compound the $^1$H-NMR spectrum data (400 MHz, CDCl$_3$) were δ/ppm=1.21-1.41 (br, 12H, alkyl chain), 1.55-1.62 (br, 2H), 2.03 (q, 2H, J=7.64 Hz, =CH—CH$_2$—CH$_2$), 3.60 (t, 2H, J=6.64 Hz, CH$_2$—CH$_2$—O—), 3.81 (t, 2H, J=9.68 Hz, —CF$_2$—CH$_2$—O—), 3.93 (q, 2H, J=9.60, HO—CH$_2$—CF$_2$), 4.92-5.01 (br, 2H, olefin), 5.78-5.85 (br, 1H, olefin).

(D) Syntheses of 14,14,16,16,17,17,19,19,20,20,22,22-dodecafluoro-3,6,9,12,15,18,21,24-octaoxatricos-34-en-1-ol (PEG4-FTEG-C11), 11,11,13,13,14,14,16,16,17,17,19,19-dodecafluoro-3,6,9,12,15,18,21-heptaoxadotriacont-31-en-1-ol (PEG3-FTEG-C11), and 8,8,10,10,11,11,13,13,14,14,16,16-dodecafluoro-3,6,9,12,15,18-hexaoxanonacos-28-en-1-ol (PEG2-FTEG-C11)

PEG4-FTEG-C11, PEG3-FTEG-C11, and PEG2-FTEG-C11 were synthesized as follows.

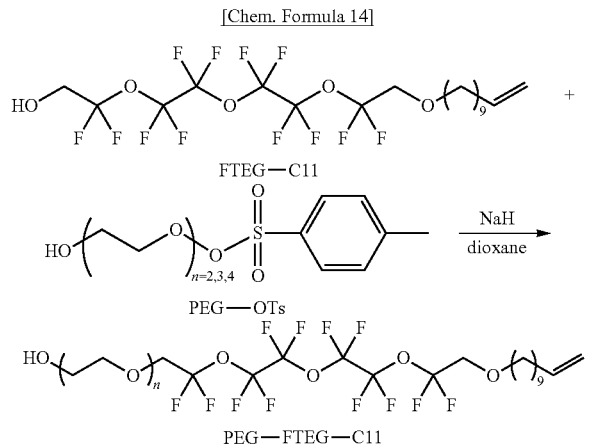

In a 100 mL-Nasu flask, 2.12 g (3.77 mmol) of FTEG-C11 obtained as above was charged and the inside of the flask was replaced with nitrogen, to which 15 mL of dioxane (anhydrous grade) was added and further 226 mg (5.66 mmol) of 60% hydrogenated sodium (NaH) was added with good stirring, and the mixture was stirred for 20 min. After white foaming subsided, a solution of 3.3 g (9.05 mmol) of PEG4-OTs obtained as above dissolved in 4 mL of dioxane was dropped, and the mixture was stirred at 50° C. overnight. After adding a small amount of methanol, the solvent was evaporated by a rotary evaporator. The residue was dissolved in 30 mL of chloroform, and washed 3 times with approx. 10 mL of a saturated saline solution. Then the organic layer was dried over sodium sulfate and concentrated under a reduced pressure. After purification by silica gel column chromatography (development: chloroform:hexane=4:1→chloroform:ethyl acetate=2:1), transparent liquid PEG4-FTEG-C11 (1.22 g, 1.65 mmol, 44%) was obtained. For the obtained compound the $^1$H-NMR spectrum data (400 MHz, CDCl$_3$) were δ/ppm=1.22-1.30 (br, 10H, alkyl chain), 1.53-1.63 (br, 5H,), 2.05 (q, 2H, J=7.76 Hz, CH$_2$=CH—CH$_2$—), 3.58-3.94 (br, 24H), 4.92-5.01 (br, 2H, olefin), 5.76-5.84 (br, 1H, olefin). Further, the result of MALDI-TOF MS analysis (m/z) was [M+Na] calcd for C$_{27}$H$_{42}$F$_{12}$O$_9$Na, 761.50. Found, 761.3129, [M+K] calcd for C$_{27}$H$_{42}$F$_{12}$O$_9$K, 777.70. Found, 777.2949.

By syntheses same as above, except that PEG3-OTs and PEG2-OTs as obtained above were used instead of PEG4-OTs, were obtained PEG3-FTEG-C11 (1.19 g, 1.71 mmol, 45%) and PEG2-FTEG-C11 (490 mg, 0.75 mmol, 28%). For the obtained PEG3-FTEG-C11 the $^1$H-NMR spectrum data (600 MHz, CDCl$_3$) were δ/ppm=1.25-1.41 (br, 13H, alkyl chain), 1.58-1.60 (br, 2H, alkyl chain), 2.04 (q, 2H, J=7.56 Hz, =CH—CH$_2$—CH$_2$), 3.59-3.94 (br, 18H, —CH$_2$—O—), 4.91-5.00 (br, 2H, olefin), 5.78-5.83 (br, 1H, olefin), and the result of MALDI-TOF MS analysis (m/z) was [M+H] calcd for C$_{25}$H$_{39}$F$_{12}$O$_8$, 695.55. Found, 695.4, [M+Na] calcd for C$_{25}$H$_{38}$F$_{12}$O$_8$Na, 717.54. Found, 717.4, [M+K] calcd for C$_{25}$H$_{38}$F$_{12}$O$_8$K, 733.65. Found, 733.4. For the obtained PEG2-FTEG-C11 the $^1$H-NMR spectrum data (400 MHz, CDCl$_3$) were δ/ppm=1.24-1.41 (br, 13H, alkyl chain), 1.55-1.60 (br, 2H, alkyl chain), 2.04 (q, 2H, J=7.68 Hz, =CH—CH$_2$—CH$_2$), 3.58-3.83 (br, 12H, —CH$_2$—O—), 3.91 (t, 2H, J=9.724, —CF$_2$—CH$_2$—O—), 4.91-5.00 (br, 2H, olefin), 5.78-5.83 (br, 1H, olefin).

(E) Syntheses of 14,14,16,16,17,17,19,19,20,20,22,22-dodecafluoro-3,6,9,12,15,18,21,24-octaoxatricos-1-ol-35-yl ethaneethionate (PEG4-FTEG-C11-SOMe), 11,11,13,13,14,14,16,16,17,17,19,19-dodecafluoro-3,6,9,12,15,18,21-heptaoxadotriacont-1-ol-32-yl ethaneethionate (PEG3-FTEG-C11-SOMe), and 8,8,10,10,11,11,13,13,14,14,16,16-dodecafluoro-3,6,9,12,15,18-hexaoxanonacos-1-ol-29-yl ethaneethionate (PEG2-FTEG-C11-SOMe)

PEG4-FTEG-C11-SOMe, PEG3-FTEG-C11-SOMe, and PEG2-FTEG-C11-SOMe were synthesized as follows.

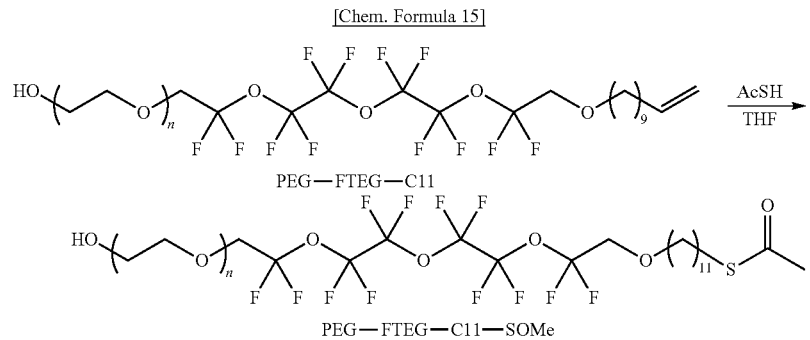

In a 100 mL-Nasu flask 1.22 g (1.65 mmol) of PEG4-FTEG-C11 obtained as above was dissolved in 15 mL of THF (anhydrous grade, unstabilized). Into this, 587 μL (8.26 mmol) of thioacetic acid (AcSH) was added with stirring and further 271 mg (1.65 mmol) of 2,2'-azobisisobutyronitrile (AIBN) was added. The solution was stirred at 100° C. at reflux for 45 min. Thereafter 10 mL of methanol was added for dilution, and the solvent was evaporated by a rotary evaporator, followed by concentration under a reduced pressure. The residue was purified by silica gel column chromatography (development: chloroform alone→chloroform:ethyl acetate=2:1) to obtain transparent liquid PEG4-FTEG-C11-SOMe (1.10 g, 1.35 mmol, 82%). For the obtained compound the $^1$H-NMR spectrum data (400 MHz, CDCl$_3$) were δ/ppm=1.24-1.32 (br, 15H, alkyl chain), 1.50-1.69 (br, 3H), 2.04 (s, 1H), 2.32 (s, 3H, CH$_3$CO—), 2.86 (t, 2H, J=7.2 Hz, —CH$_2$—SAc), 3.58-3.83 (br, 21H), 3.92 (t, 2H, J=8.0 Hz, —CF$_2$—CH$_2$—O—). While the result of MALDI-TOF MS analysis (m/z) for the obtained compound was [M+Na] calcd for C$_{29}$H$_{46}$F$_{12}$O$_{10}$SNa, 837.71. Found, 837.0123.

By syntheses same as above, except that PEG3-FTEG-C11 and PEG2-FTEG-C11 were used instead of PEG4-FTEG-C11, 0.99 g (1.28 mmol, 77%) of PEG3-FTEG-C11-SOMe and 520 mg (0.71 mmol, 97%) of PEG2-FTEG-C11-SOMe were obtained.

(F) Syntheses of PEG4-FTEG-C11-SH, PEG3-FTEG-C11-SH, and PEG2-FTEG-C11-SH

PEG4-FTEG-C11-SH, PEG3-FTEG-C11-SH, and PEG2-FTEG-C11-SH were synthesized as follows.

at 50° C. for 2 hours. Thereafter approx. 1 g of Dowex (50WX 8-200, by The Dow Chemical Company) washed with methanol was added and the solvent was evaporated by a rotary evaporator, followed by concentration under a reduced pressure. The residue dissolved in chloroform was spread over a PLC plate (PLC glass plate silica gel 60F254, 0.5 mm, by Merck & Co., Inc., USA) for purification (development solvent: ethyl acetate+methanol) to obtain 460 mg (0.59 mmol, 44%) of white crystalline PEG4-FTEG-C11-SH. For the obtained compound the $^1$H-NMR spectrum data (400 MHz, CDCl$_3$) were δ/ppm=1.27-1.35 (br, 16H, alkyl chain), 1.57-1.60 (br, 4H, alkyl chain), 3.58-3.83 (br, 22H), 3.93 (t, 2H, J=10 Hz). While, the result of MALDI-TOF MS analysis (m/z) for the obtained compound was [M+] calcd for C$_{27}$H$_{44}$F$_{12}$O$_9$S, 772.68. Found, 772.45, [M+Na] calcd for C$_{27}$H$_{44}$F$_{12}$NaO$_9$S, 795.67. Found, 794.51.

By syntheses same as above, except that PEG3-FTEG-C11-SOMe and PEG2-FTEG-C11-SOMe were used instead of PEG4-FTEG-C11-SOMe, 360 mg (0.494 mmol, 39%) of PEG3-FTEG-C11-SH, or 140 mg (0.204 mmol, 29%) of PEG2-FTEG-C11-SH was obtained.

[Chem. Formula 16]

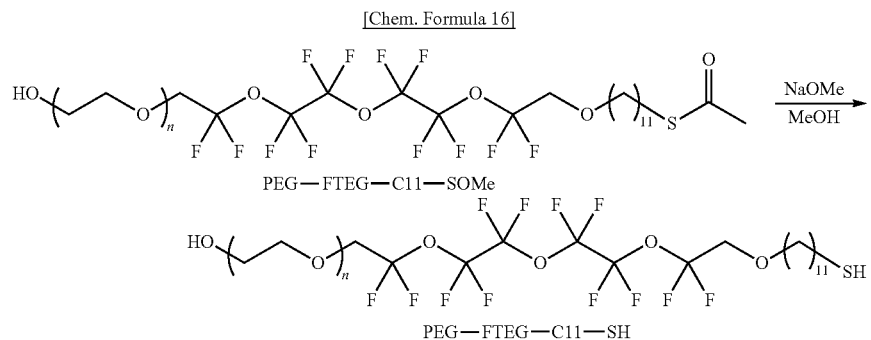

In a 100 mL-Nasu flask 1.10 g (1.35 mmol) of PEG4-FTEG-C11-SOMe obtained as above was dissolved in 20 mL of methanol (anhydrous grade) with stirring. Into this, 26 μL (0.135 mmol) of a 28% methanol solution of sodium methoxide (NaOMe) was added and the solution was stirred PEG4-FTEG-C11-SH, PEG3-FTEG-C11-SH, and PEG2-FTEG-C11-SH as surface modifiers for a metal core were obtained as above. The structural formulas for the respective compounds were as follows.

[Chem. Formula 17]

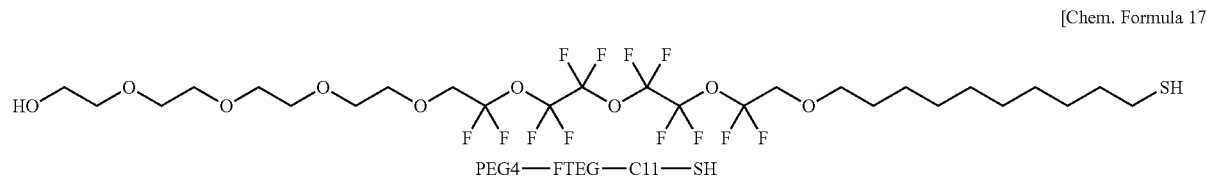

[Chem. Formula 18]

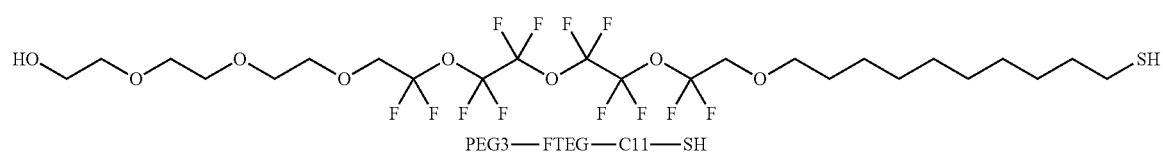

[Chem. Formula 19]

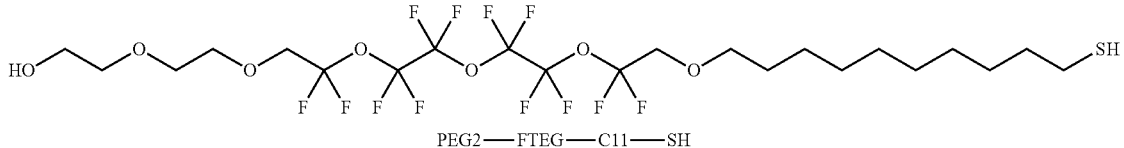

PEG2—FTEG—C11—SH (Ligand Exchange Reaction and Self Organization)

In a 1.5 mL-microtube, 1 mL (17 pmol/mL) of a 5 nm gold-citric acid colloidal solution (Gold Colloid 5 nm, by British BioCell International) was placed and centrifuged at 10,000 rpm and 4° C. for 90 min. The supernatant was removed using a micropipetter to prepare a gold-citric acid colloidal solution concentrated approx. 100-fold. In another 1.5 mL-microtube 2 μmol of PEG4-FTEG-C11-SH (dissolved in methanol) obtained as above was placed and methanol was air-dried, to which 490 μL of THF was added to dissolve PEG4-FTEG-C11-SH. While the 1.5 mL-microtube containing PEG4-FTEG-C11-SH was being exposed to ultrasonic waves (Apparatus used: ultrasonic washer 1510J-MT, by Yamato Scientific Co., Ltd.) in a water bath, 10 μL of the gold-citric acid colloidal solution prepared as above was dropped. After exposed for another 20 min to ultrasonic waves same as above, the mixture was stirred at normal temperature for 2 days. At this stage, the concentration of gold in the reaction solution was almost same as the concentration of the gold-citric acid colloidal solution before concentration (=17 pmol/mL), and the number of molecules of PEG4-FTEG-C11-SH was approx. 75-fold the total number of bonding sites of gold fine particles in the solution. During the above, the color of the solution changed from red to purple. The reaction product was then centrifuged at 10,000 rpm and 4° C. for 5 min. The supernatant was removed with a micropipetter, and 500 μL of THF was added to the pellet. By repeating a centrifugation, the supernatant was removed. After adding 200 μL of THF to the pellet, the mixture was exposed to ultrasonic waves as described above. Thus, a THF solution of a fluorinated thiol (PEG4)-presenting gold particle aggregate was obtained.

Similarly, by syntheses same as above, except that PEG3-FTEG-C11-SH and PEG2-FTEG-C11-SH obtained as above were used instead of PEG4-FTEG-C11-SH, a THF solution of a fluorinated thiol (PEG3)-presenting gold particle aggregate and a THF solution of a fluorinated thiol (PEG2)-presenting gold particle aggregate were obtained.

(Size Distribution of Fluorinated Thiol-Presenting Gold Particle Aggregate in Solution)

Using the THF solution of the fluorinated thiol (PEG4)-presenting gold particle aggregate, the THF solution of the fluorinated thiol (PEG3)-presenting gold particle aggregate, and the THF solution of the fluorinated thiol (PEG2)-presenting gold particle aggregate obtained as above, the dynamic light scattering (DLS) of each particle aggregate in a solution was measured. The measurements were carried out with Delsa Nano HC (by Beckman Coulter, Inc.) in THF at 20° C. The results are shown in FIG. 1. The DLS peak values for the respective aggregates were confirmed to be approx. 50 to 70 nm.

(Observation of Fluorinated Thiol-Presenting Gold Particle Aggregate)

The THF solution of the fluorinated thiol (PEG4)-presenting gold particle aggregate obtained as above, was spread over a grid mesh for a TEM electron microscope (STEM100 Cu grid, with elastic carbon supporting film, grid pitch 100 μm) and air-dried. The fluorinated thiol (PEG4)-presenting gold particle aggregate was observed with an electron microscope (HD-2000, by Hitachi, Ltd.) at an acceleration voltage of 200 kV. The results are shown in FIGS. 2A to D. From the SEM image of FIG. 2B it was confirmed that a surface of a spherical structure was covered with particles, and that a 3-dimensional spherical structure was formed. Further, it was confirmed from the TEM image of FIG. 2C that the inside of the spherical structure was seen through, and also confirmed by combining the result of the SEM image that a hollow spherical structure was formed. While, the diameter of the spherical structure was approx. 100 nm. Further from the TEM image of FIG. 2D, the existence of a spherical structure with the diameter of approx. 200 to 400 nm was also confirmed. From the above, formation of a 3-dimensional spherical structure of the fluorinated thiol (PEG4)-presenting particle aggregate was confirmed in the dry state.

(Measurement of Absorbance for THF Solution of Fluorinated Thiol-Presenting Gold Particle Aggregate)

Figure 3:
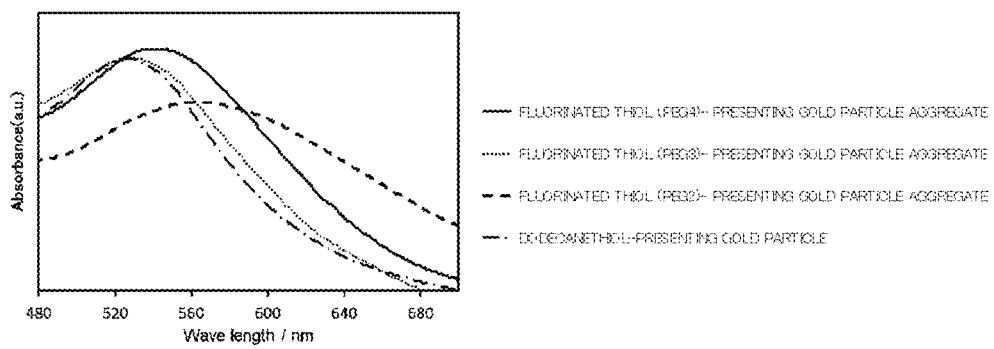
FIG. 3 is a graph showing the absorbance of particle aggregates according to an Example of the present invention.

In order to confirm whether a particle aggregate was formed in a solution, the absorbance of the THF solution of the fluorinated thiol (PEG4)-presenting gold particle aggregate, the THF solution of the fluorinated thiol (PEG3)-presenting gold particle aggregate, and the THF solution of the fluorinated thiol (PEG2)-presenting gold particle aggregate obtained as above, and the absorbance of a THF solution of a dodecanethiol-presenting gold particle prepared as a control were measured at the substantially same concentration of a gold nanoparticle in each solution with an ultraviolet and visible spectrophotometer (UV-1650PC, by Shimadzu Corporation). In this regard, the dodecanethiol-presenting gold particle does not have a fluorinated segment and a PEG segment. The results are shown in FIG. 3 and Table 1. It was confirmed that compared to the absorbance of the THF solution of the dodecanethiol-presenting gold particle, the absorbance of any of the THF solution of the fluorinated thiol (PEG4)-presenting gold particle aggregate, the THF solution of the fluorinated thiol (PEG3)-presenting gold particle aggregate, and the THF solution of the fluorinated thiol (PEG2)-presenting gold particle aggregate was shifted to the long-wavelength side. From this it was confirmed that a particle aggregate was formed in a solution.

TABLE 1

| Surface thiol | $\lambda max(nm)$ |
|---|---|
| Fluorinated thiol (PEG4) | 541 |
| Fluorinated thiol (PEG3) | 528 |
| Fluorinated thiol (PEG2) | 559 |
| Dodecanethiol (Dispersion) | 520 |

(Measurement of Coverage with Fluorinated Thiol-Presenting Gold Particle Aggregate)

Using the THF solution of the fluorinated thiol (PEG2)-presenting gold particle aggregate obtained as above, the coverage of PEG2-FTEG-C11-SH over a surface of a gold particle as a metal core was measured. For measurement an ICP emission analyzer (ICPE-9000, by Shimadzu Corporation) was used.

The content ratio of gold atom to sulfur atom was determined by dissolving the THF solution of the fluorinated thiol (PEG2)-presenting gold particle aggregate obtained as above in aqua regia and burning the same in high-frequency inductively coupled plasma. From the content ratio and based on the number of gold atoms presented on a surface, the coverage was calculated. As the result, the coverage was 58.1%.

(X-Ray Small-Angle Scattering (SAXS) Analysis)

To reconfirm that the particle aggregate obtained as above was a hollow body, an X-ray small-angle scattering (SAXS) analysis was conducted on the THF solution of the fluorinated thiol (PEG2)-presenting gold particle aggregate obtained as above. Specifically, the X-ray scattering intensity of the particle aggregate based on found values and the X-ray scattering intensity of a core-shell model (fitting) were compared to examine whether the SAXS scattering profiles coincide. For measuring the X-ray scattering intensity of the particle aggregate an X-ray diffractometer NANO-Viewer (by Rigaku Corporation) was used (measurement conditions: camera length: 600 mm, exposure time: 3 hours, detection: imaging plate, X-ray wavelength: 0.1542 nm). For analysis, an analysis software of NANO-Solver (Ver 3.4) (by Rigaku Corporation) was used.

A SAXS analysis will be described below. X-ray scattering intensity (I (q)) depends on the shape and the size of a scatterer (reflecting a form factor (F (q)) and the distance between scatterers (reflecting a structure factor (S (q)), and is expressed by the following formula:

$$I(q)=|F(q)|^2 S(q) \quad q=4\pi/\lambda \sin 2\theta/2 \qquad \text{[Num. Formula 1]}$$

(q: scattering vector, $\lambda$: X-ray wavelength, $\theta$: one-half of angle between scattered beam and incoming beam)

In this case only a form factor is considered. In the case that a scatterer model is a core-shell model, the form factor is represented by the following formula.

$$F^{core\_shell}(q,R,d)=(\rho_2-\rho_1)4\pi/q^3(\sin(qR)-qR\cos(qR))+\\(\rho_1-\rho_0)4\pi/q^3(\sin q(R+d)-q(R+d)\cos(q(R+d))) \qquad \text{[Num. Formula 2]}$$

Figure 4:
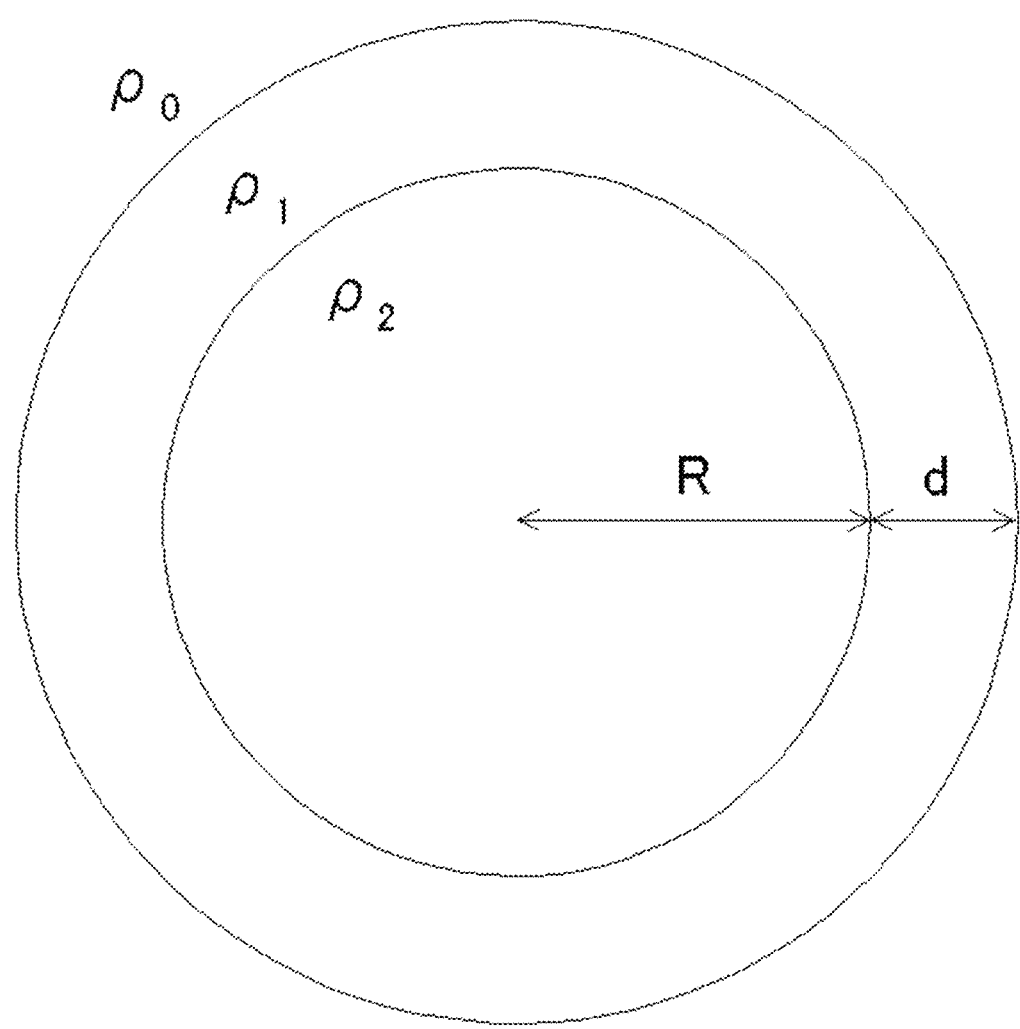
FIG. 4 is a figure showing a core-shell model to be used for fitting in a SAXS analysis.

(R: internal radius of shell, d: thickness of shell, $\rho_0$: density outside shell, $\rho_1$: density of shell, $\rho_2$: density inside shell, (FIG. 4))

The respective parameters were fixed as follows: $\rho_0$=0.89 g/cm$^3$ (THF), $\rho_1$=19.32 g/cm$^3$ (Au), $\rho_2$=0.89 g/cm$^3$ (THF) and d=10 nm.

Figure 5:
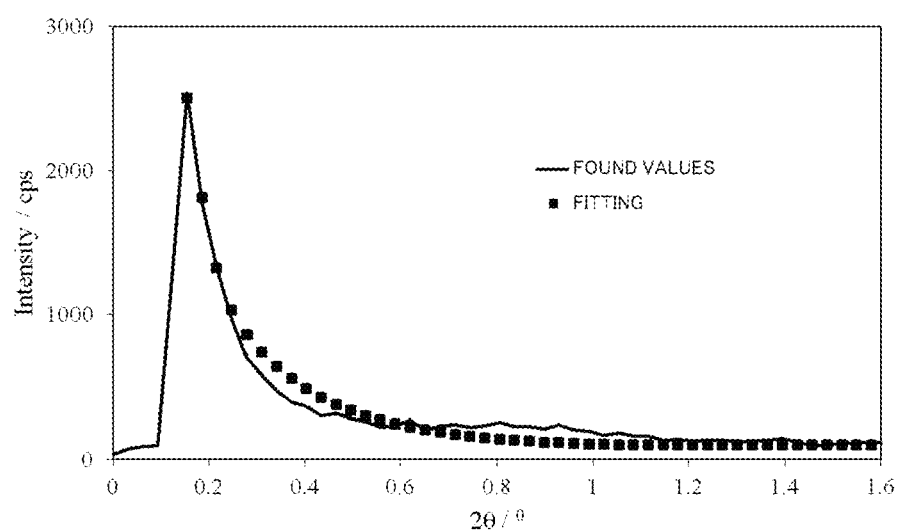
FIG. 5 is a graph showing X-ray scattering intensity in a SAXS analysis.

In FIG. 5, with respect to the X-ray scattering intensity for the particle aggregate, a comparison between a found value curve and a fitting curve is shown. The found value curve and the fitting curve substantially coincided. From this, it was confirmed that the particle aggregate was a hollow body.

Comparative Example

FTEG-C11-SH not having a PEG segment, or PEG4-C11-SH not having a fluorinated segment was mixed with a 5 nm gold-citric acid colloidal solution respectively, followed by a ligand exchange reaction same as above, to yield a gold particle solution not having a PEG segment, or a gold particle solution not having a fluorinated segment. The gold particle not having a PEG segment and the gold particle not having a fluorinated segment are shown respectively as follows:

[Chem. Formula 20]

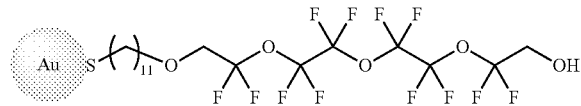

Gold particle not having a PEG segment

[Chem. Formula 21]

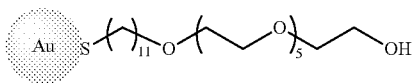

Gold particle not having a fluorinated segment

Figure 6A:
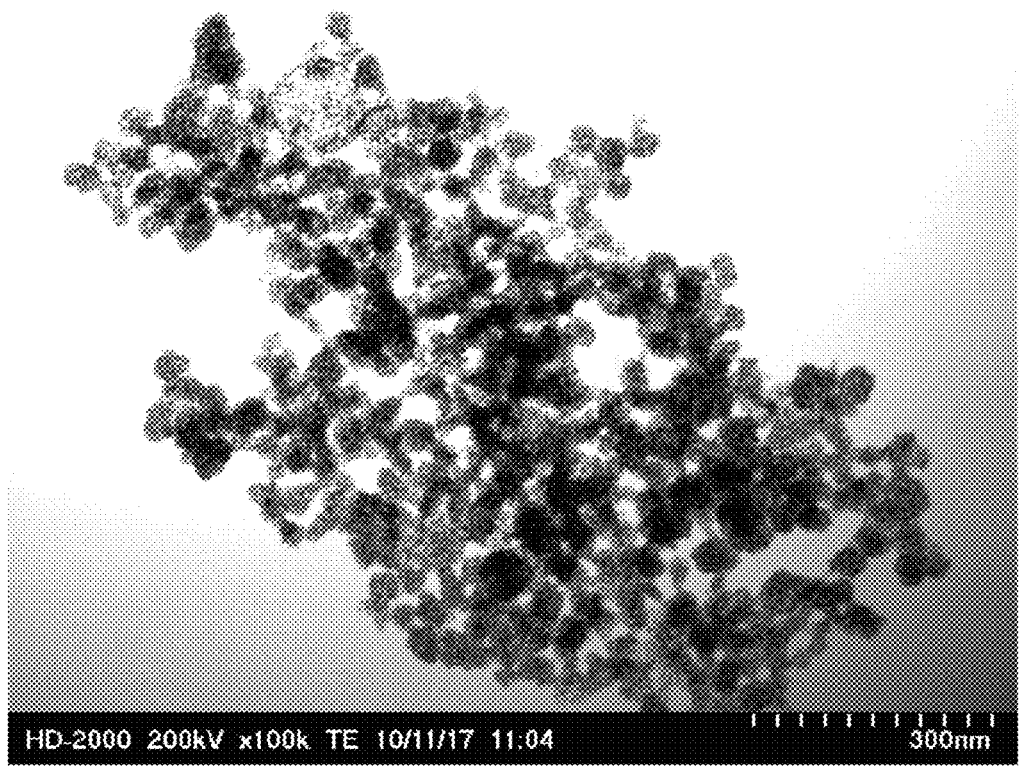
FIG. 6A is a picture showing an electron microscopic image of gold particles not having a PEG segment.
Figure 6B:
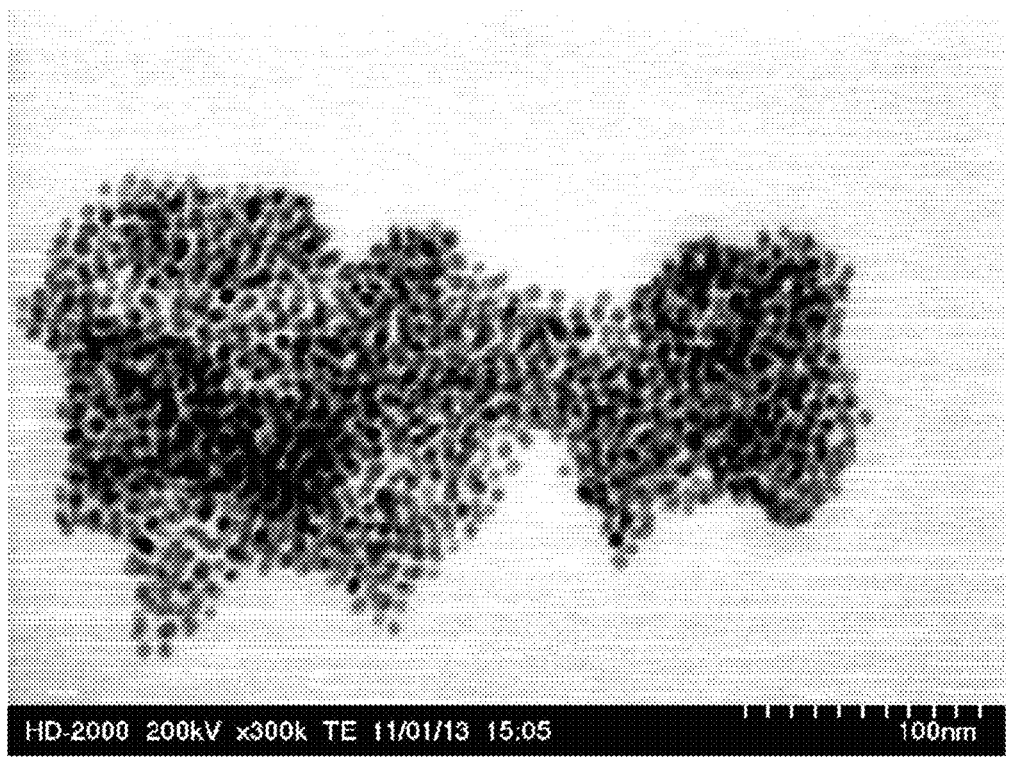
FIG. 6B is a picture showing an electron microscopic image of gold particles not having a fluorinated segment.

The respective particles were observed by use of an electron microscope as above. The results are shown in FIGS. 6A and 6B. FIG. 6A is an electron microscopic image of a gold particle not having a PEG segment, and FIG. 6B is an electron microscopic image of a gold particle not having a fluorinated segment. It was confirmed that both the particles did not form a particle aggregate. From this it became clear that by using a surface modifier provided with a fluorinated segment (first segment) and a PEG segment (second segment) self organization of particles was attained and a particle aggregate could be yielded.

Example 2

The Raman active scattering enhancement activity of a hollow particle aggregate according to the present invention on a substrate was investigated.

Figure 7:
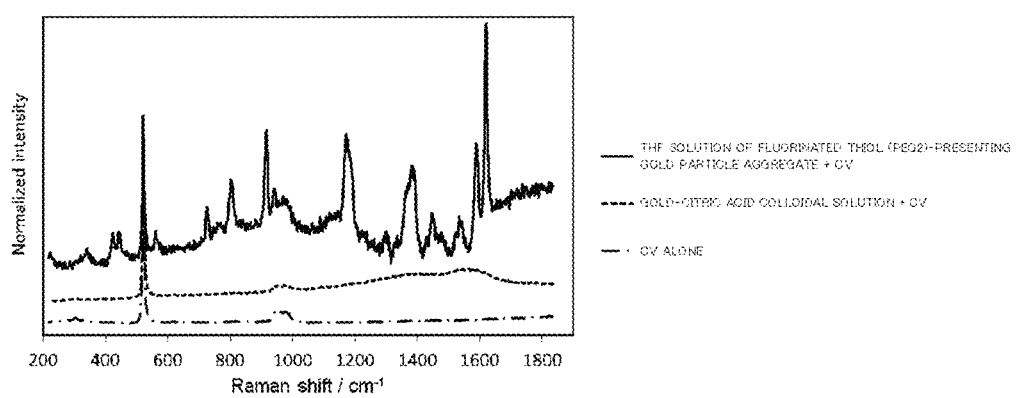
FIG. 7 is a graph showing Raman spectra of particle aggregates on a substrate according to an Example of the present invention.

To 80 µL of the THF solution of the fluorinated thiol (PEG2)-presenting gold particle aggregate obtained in Example 1, 10 µL of crystal violet (CV) was added and the mixture was dissolved in THF. After 1 hour from the dissolution, the solution was dropped on a silicon substrate (silicon/wafer $\phi$100×0.5 mm, Low, 111, N-type, by The Nilaco Corporation) to dry up the solvent, for which the Raman shift was measured under conditions of: excitation wavelength: 532 nm, objective lens: 50×, laser output: 10%, integration time: 5 sec, and measurement apparatus: Raman microscope system in Via Reflex (by Renishaw). As a control the Raman shift was measured by dropping the 5 nm gold-citric acid colloidal solution used in Example 1 and CV on a silicon substrate same as above. As the result, as shown in FIG. 7, with respect to the 5 nm gold-citric acid colloidal solution, a peak originated from CV was not detected, but with respect to the THF solution of the fluorinated thiol (PEG2)-presenting gold particle aggregate, peaks originated from CV were detected. From this it was confirmed that the fluorinated thiol (PEG2)-presenting gold particle aggregate enhanced the Raman scattering activity. In other words, it was confirmed that the fluorinated thiol (PEG2)-presenting gold particle aggregate, when the same was spread over a substrate, enhanced light absorption by localized surface plasmon resonance.

Example 3

The Raman active scattering enhancement activity of a hollow particle aggregate according to the present invention in a solution was investigated.

The following samples (a) to (d) were prepared respectively.

(a): Only CV was added to THF (CV concentration: $1 \times 10^{-5}$ μM).

(b): To the THF solution of the dodecanethiol-presenting gold particle obtained in Example 1, CV was added (CV concentration: $1 \times 10^{-5}$ μM).

(c): To the THF solution of the fluorinated thiol (PEG2)-presenting gold particle aggregate obtained in Example 1, CV was added (CV concentration: $1 \times 10^{-5}$ μM).

(d): A CV encapsulated particle aggregate, in which CV was encapsulated in a hollow part of the fluorinated thiol (PEG2)-presenting gold particle aggregate, was prepared. Specifically, a CV encapsulated particle aggregate was prepared same as in Example 1 (ligand exchange reaction and self organization), except that the THF used in Example 1 was replaced with the (a) above.

Figure 8:
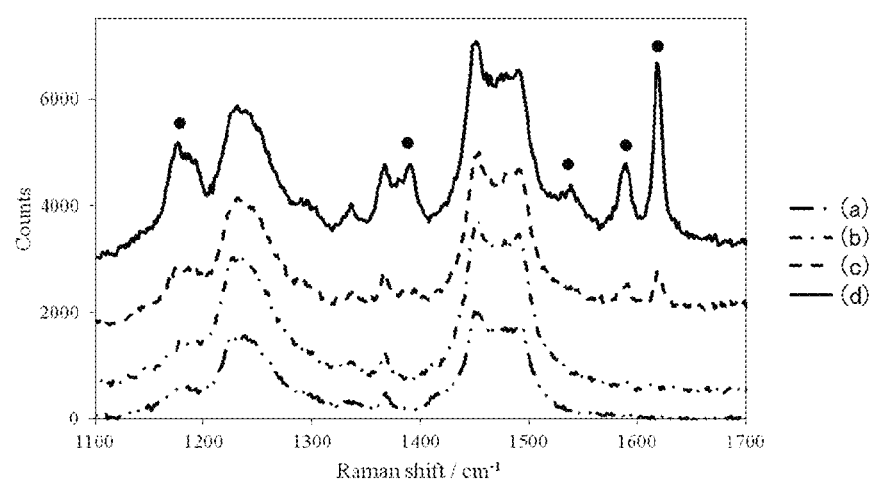
FIG. 8 is a graph showing Raman spectra of particle aggregates in a solution according to an Example of the present invention.

Using the samples (a) to (d), the Raman shift of CV in a THF solution ($1 \times 10^{-5}$ μM) was measured under conditions: excitation wavelength: 532 nm, objective lens: 20×, laser output: 5%, integration time: 10 sec, and measurement apparatus: Raman microscope system in Via Reflex (by Renishaw). The results are shown in FIG. 8. Round dots in FIG. 8 represent Raman signals originated from CV. With respect to (c) and (d) the Raman scattering activity was enhanced compared to (a) and (b). Further, with respect to (d) the Raman scattering activity was further enhanced compared to (c).

From the above it became clear that a fluorinated thiol (PEG2)-presenting gold particle aggregate, when existing in a solution, enhanced the light absorption by localized surface plasmon resonance. It was further demonstrated, that, by encapsulating CV in a hollow part of the fluorinated thiol (PEG2)-presenting gold particle aggregate, a higher light absorption enhancement effect was able to be obtained.

Example 4

Formation of a spherical structure was compared by replacing a solvent for the fluorinated thiol (PEG4)-presenting gold particle aggregate with various solvents.

The THF solution of the fluorinated thiol (PEG4)-presenting gold particle aggregate obtained in Example 1 was centrifuged at 10,000 rpm and 4° C. for 5 min. After removing the supernatant with a micropipetter, each of the replacement solvents of ethyl acetate, dichloromethane, acetone, butanol, methanol, and dimethylformamide (DMF) was added to the pellet and the mixture was exposed to ultrasonic waves for approx. 10 sec as above to replace the solvent with each replacement solvent. The product was dropped on a grid mesh for a TEM electron microscope as above, dried for half a day or longer, and observed with an electron microscope as above. The results are shown in Table 2. In acetone and DMF spherical structures and collapsed spherical structures were mixed and in the visual field approx. 50% of the total was visually recognized as spherical structures. In ethyl acetate, dichloromethane, butanol, and methanol, spherical structures were maintained well. From the above it became clear that a hollow particle aggregate according to the present invention was able to maintain the shape, into which a particle aggregate was formed, stably also in a replacement solvent.

TABLE 2

| Replacement solvent | Stability of sphere | DLS peak value(nm) |
|---|---|---|
| Ethyl acetate | Good | 61.8 |
| Dichloromethane | Good | 74.7 |
| Acetone | Average | 61.8 |
| Butanol | Good | 67.9 |
| Methanol | Good | 61.8 |
| DMF | Average | 51.2 |

Example 5

The stability of a fluorinated thiol (PEG2)-presenting gold particle aggregate embedded in an epoxy resin was evaluated.

A fluorinated thiol (PEG2)-presenting gold particle aggregate was embedded in an epoxy resin by mixing 50 μL of the THF solution of the fluorinated thiol (PEG2)-presenting gold particle aggregate obtained in Example 1 and 450 μL of an epoxy resin (Epok812, Okenshoji Co., Ltd.), and curing the same at 60° C. for 12 hours. The color of the epoxy resin before the curing reaction was purple, and the color of the epoxy resin stored at room temperature for 1 month after the curing reaction was still purple.

From the above it became clear that a fluorinated thiol (PEG2)-presenting gold particle aggregate in a state embedded in an epoxy resin was able to maintain the state stably into which the particle aggregate was formed, and that the aggregate was distributed homogeneously in an epoxy resin. Consequently, it is conceivable to use the resin as a light sensing material.

As described above, a hollow particle aggregate, a light enhancing element, and an apparatus utilizing a photochemical reaction according to the present invention is able to be produced by a simple operation, and is superior in a light enhancing effect. Further, a production method for a hollow particle aggregate according to the present invention is able to be exercised by a simple operation.

Various embodiments of and modification to the present invention are possible without departing from the spirit and scope in broader sense of the present invention. While the aforedescribed embodiments are intended to explain the present invention but not to limit the scope the present invention. Namely, the scope of the present invention is defined not by the embodiments but by the CLAIMS. And any variations made within the scope of the CLAIMS and within the scope of the equivalent meaning of the invention are deemed as within the scope of the present invention.

This application claims priority based on Japanese Patent Application No. 2011-036468 filed on 22 Feb. 2011. The entire DESCRIPTION, CLAIMS, and DRAWINGS of Japanese Patent Application No. 2011-036468 are incorporated by reference herein.

The invention claimed is:

1. A hollow particle aggregate formed by aggregating a plurality of self-organizable particles, wherein each self-organizable particle comprises a metal core which is modified by at least one surface modifier, wherein each surface modifier comprises:

a first segment comprising $R_f$, and wherein $R_f$ is selected from the set consisting of the general formulas (1) and (2),

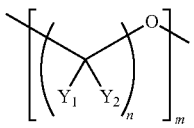

(1)

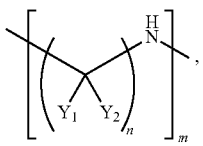

(2)

an optionally branched fluorinated alkylene glycol group, an optionally branched fluorinated alkylene group, or an optionally branched fluorinated azaalkylene group;
wherein each of $Y_1$ and $Y_2$ represents a hydrogen atom or a fluorine atom, and at least one of $Y_1$ and $Y_2$ is a fluorine atom, m represents an integer of 1 to 12, and n represents an integer of 1 to 6;
a second segment comprising at least one hydrophilic group which binds to a first end of a main chain of the first segment; and
a functional group X that binds directly or indirectly to a second end of the main chain of the first segment and is able to bind to the metal core, wherein the functional group X is a thiol group, a cyano group, a dithiol group, an amino group, or an isocyano group.

2. The hollow particle aggregate according to claim 1, wherein the surface modifier is expressed by a general formula $R_t$—$(R_h$—$O)_l$—$R_f$—$R_a$—X,
wherein $R_t$ represents a hydrogen atom, a hydroxy group, a C1 to C4 alkoxyl group, or a C1 to C4 alkyl group;
$R_h$ represents an optionally branched C2 to C6 alkylene group,
$R_a$ represents a C3 to C18 normal chain alkyl, a C3 to C18 branched alkyl, or a C3 to C18 aralkyl; l represents an integer of 1 to 12; and —$(R_h$—$O)_l$— includes a cyclic group.

3. The hollow particle aggregate according to claim 1, wherein the aggregate is a near-spherical body.

4. The hollow particle aggregate according to claim 3, wherein the diameter of the near-spherical body is 30 to 400 nm.

5. The hollow particle aggregate according claim 1, wherein the coverage of a surface of the metal core by the surface modifier for a metal core is 20% or more.

6. The hollow particle aggregate according to claim 1, wherein the metal core comprises gold, platinum, silver, copper, iron, or a semiconductor quantum dot.

7. A light enhancing element comprising the hollow particle aggregate according claim 1.

8. A light sensing device comprising the light enhancing element according to claim 7.

9. A production method for a particle aggregate comprising mixing a solvent with a metal core comprising a ligand on a surface and a surface modifier comprising a first segment comprising $R_f$, and wherein $R_f$ is selected from the set consisting of the general formulas 1 and 2,

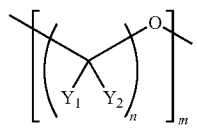

(1)

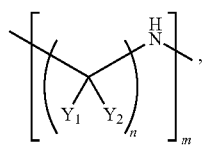

(2)

an optionally branched fluorinated alkylene glycol group, an optionally branched fluorinated alkylene group, or an optionally branched fluorinated azaalkylene group;
wherein each of $Y_1$ and $Y_2$ represents a hydrogen atom or a fluorine atom, and at least one of $Y_1$ and $Y_2$ is a fluorine atom, m represents an integer of 1 to 12, and n represents an integer of 1 to 6;
a second segment comprising at least one hydrophilic group which binds to a first end of a main chain of the first segment; and a functional group X that bonds directly or indirectly to a second end of the main chain of the first segment and is able to bond to the metal core, wherein the functional group X is a thiol group, a cyano group, a dithiol group, an amino group, or an isocyano group.

10. The production method for a particle aggregate according to claim 9, wherein the surface modifier is expressed by a general formula $R_t$—$(R_h$—$O)_l$—$R_f$—$R_a$—X,
wherein $R_t$ represents a hydrogen atom, a hydroxy group, a C1 to C4 alkoxyl group, or a C1 to C4 alkyl group,
$R_h$ represents an optionally branched C2 to C6 alkylene group,
$R_a$ represents a C3 to C18 normal chain alkyl, a C3 to C18 branched alkyl, or a C3 to C18 aralkyl; l represents an integer of 1 to 12; and —$(R_h$—$O)_l$— includes a cyclic group.

11. The production method for a particle aggregate according to claim 9, further comprising replacing the solvent with a replacement solvent.

* * * * *